(12) United States Patent
Terumoto et al.

(10) Patent No.: US 9,113,793 B2
(45) Date of Patent: Aug. 25, 2015

(54) PULSE WAVE SENSOR

(75) Inventors: Koji Terumoto, Kyoto (JP); Daisuke Niwa, Kyoto (JP); Tsuyoshi Satomi, Kyoto (JP); Kazuhiro Oguchi, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 617 days.

(21) Appl. No.: 13/295,241

(22) Filed: Nov. 14, 2011

(65) Prior Publication Data

US 2012/0150047 A1 Jun. 14, 2012

(30) Foreign Application Priority Data

Dec. 10, 2010 (JP) ................................ 2010-275574
Dec. 10, 2010 (JP) ................................ 2010-275590
Jan. 7, 2011 (JP) ................................ 2011-002422

(51) Int. Cl.
| | |
|---|---|
| *A61B 5/02* | (2006.01) |
| *A61B 5/024* | (2006.01) |
| *A61B 5/1455* | (2006.01) |
| *A61B 5/00* | (2006.01) |

(52) U.S. Cl.
CPC ......... *A61B 5/02427* (2013.01); *A61B 5/14552* (2013.01); *A61B 5/681* (2013.01); *A61B 5/6803* (2013.01); *A61B 5/6814* (2013.01); *A61B 5/6826* (2013.01); *A61B 5/02007* (2013.01); *A61B 5/02405* (2013.01); *A61B 5/4815* (2013.01); *A61B 2562/0219* (2013.01); *A61B 2562/0233* (2013.01); *A61B 2562/0238* (2013.01); *A61B 2562/0247* (2013.01); *A61B 2562/185* (2013.01)

(58) Field of Classification Search
CPC . A61B 5/681; A61B 5/02438; A61B 5/02416
USPC .......................................... 600/503
See application file for complete search history.

(56) References Cited

U.S. PATENT DOCUMENTS

| | | | |
|---|---|---|---|
| 5,228,449 A * | 7/1993 | Christ et al. ................... | 600/504 |
| 5,431,170 A | 7/1995 | Mathews | |
| 6,198,951 B1 | 3/2001 | Kosuda et al. | |
| 6,334,850 B1 | 1/2002 | Amano et al. | |
| 7,470,234 B1 * | 12/2008 | Elhag et al. .................... | 600/485 |
| 2002/0095092 A1 * | 7/2002 | Kondo et al. .................. | 600/503 |
| 2003/0166994 A1 | 9/2003 | Ooshima et al. | |
| 2003/0236100 A1 | 12/2003 | Fujieda et al. | |
| 2004/0193063 A1 | 9/2004 | Kimura et al. | |
| 2005/0165323 A1 * | 7/2005 | Montgomery et al. ........ | 600/544 |
| 2005/0187447 A1 * | 8/2005 | Chew et al. .................... | 600/323 |

(Continued)

FOREIGN PATENT DOCUMENTS

| | | |
|---|---|---|
| JP | 60-135029 | 7/1985 |
| JP | H03-013106 | 2/1991 |

(Continued)

*Primary Examiner* — Etsub Berhanu
(74) *Attorney, Agent, or Firm* — Fish & Richardson P.C.

(57) ABSTRACT

Among the technical characteristics disclosed in this specification, the pulse wave sensor with one of the technical characteristic includes a construction to detect the pulse wave at a wrist (i.e., a construction to measure the pulse wave to be worn at the wrist). To be more concrete, the pulse wave sensor includes a measurement unit to measure the pulse wave, a power source unit to supply power to the measurement unit, a cable to connect between the measurement unit and the power source unit electrically, and a armlet type housing to contain the measurement unit, the power source unit, and the cable.

15 Claims, 34 Drawing Sheets

(56) References Cited

U.S. PATENT DOCUMENTS

| | | | |
|---|---|---|---|
| 2005/0234351 A1* | 10/2005 | Nishii et al. | 600/503 |
| 2006/0122520 A1* | 6/2006 | Banet et al. | 600/503 |
| 2006/0224054 A1 | 10/2006 | Moriya et al. | |
| 2007/0191719 A1* | 8/2007 | Yamashita et al. | 600/503 |
| 2008/0125664 A1 | 5/2008 | Sakai et al. | |
| 2009/0198110 A1 | 8/2009 | Tamai et al. | |
| 2010/0056934 A1 | 3/2010 | Cho et al. | |
| 2010/0114132 A1* | 5/2010 | Piccionelli et al. | 606/157 |

FOREIGN PATENT DOCUMENTS

| | | |
|---|---|---|
| JP | 5-68712 | 3/1993 |
| JP | 05-212016 | 8/1993 |
| JP | 5-506802 | 10/1993 |
| JP | H07-299043 | 11/1995 |
| JP | 2003-144405 | 5/2003 |
| JP | 2003-309495 | 10/2003 |
| JP | 2004-261366 | 9/2004 |
| JP | 2005-28157 | 2/2005 |
| JP | 2008-132012 | 6/2006 |
| JP | 2006-271896 | 10/2006 |
| JP | 2006-312010 | 11/2006 |
| JP | 3882204 | 11/2006 |
| JP | 2007-209428 | 8/2007 |
| JP | 2007-215869 | 8/2007 |
| JP | 2007-319233 | 12/2007 |
| JP | 2007-330638 | 12/2007 |
| JP | 2008-220723 | 9/2008 |
| JP | 2008-245943 | 10/2008 |
| JP | 2008-272085 | 11/2008 |
| JP | 2009-005721 | 1/2009 |
| JP | 2009-039568 | 2/2009 |
| JP | 2009-153550 | 7/2009 |
| JP | 2009-178381 | 8/2009 |
| JP | 2010-051790 | 3/2010 |
| WO | 02/062222 | 8/2002 |

* cited by examiner

<PATTERN A>

<PATTERN B>

<PATTERN C>

<PATTERN D>

PULSE WAVE SENSOR

CROSS-REFERENCE TO RELATED APPLICATIONS

This application claims the benefit of priority of Japanese patent application No. 2010-275574 (filing date: Dec. 10, 2010) and No. 2010-275590 (filing date: Dec. 10, 2010) and No. 2011-002422 (filing date: Jan. 7, 2011), which are incorporated herein by reference in their entirety.

BACKGROUND OF THE INVENTION

1. Field of the Invention

This invention relates to a pulse wave sensor.

2. Description of Related Art

Conventionally, the pulse wave sensor is a construction to measure the pulse wave by means of a light emitting portion to emit a light to a fingertip of the examinee, and a light receiving portion to detect an intensity of the light penetrates through a living body. For example, with respect to the pulse wave sensor of the conventional construction, as illustrated in FIG. 15, it has a construction to measure the pulse wave at fingertip of the examinee. Moreover, with respect to the conventional pulse wave sensor, it has a construction to transmit the measurement data to the main CPU [Central Processing Unit] timely and to analyzes or stores the measurement data at main CPU side. Moreover, the conventional pulse wave sensor has a construction to connect with the main CPU by wire.

In addition, as other examples of the conventional technique related to the aforementioned technique, Japanese patent publication No. H05-212016 and international publication No. 2002/062222 can be listed.

However, with respect to the conventional construction to detect the pulse wave at the fingertip of the examinee, it is required to restrain a behavior of the examinee not to drop the pulse wave sensor from the fingertip during the measurement. Therefore, though the pulse wave can be measured for short period (e.g., from few minutes to few hours), it is difficult to perform a continuous pulse wave measurement for long period (e.g., from few days to few months).

Moreover, with respect to the conventional pulse wave sensor, there is a problem as the pulse wave can not be measured successfully according to an effect of noise component caused by a movement or vibration of the examinee (referred as "motion noise" below).

SUMMARY OF THE INVENTION

In consideration of the aforementioned problems discovered by the inventors of this application, a purpose of this invention is to provide a pulse wave sensor which can measure the pulse wave without restricting a behavior of the examinee, or to provide a pulse wave sensor which can measure the pulse wave accurately by reducing an effect of the motion noise.

The pulse wave sensor disclosed in this specification includes a construction to measure a pulse wave at a wrist (i.e., construction 1-1).

In addition, the pulse wave sensor in accordance with the construction 1-1 is an armlet construction to be worn on the wrist and to measure the pulse wave (i.e., construction 1-2).

Moreover, the pulse wave sensor in accordance with the construction 1-2 includes a measurement unit to measure the pulse wave, a power source unit to supply power to the measurement unit, a cable to connect between the measurement unit and the power source unit electrically, and an armlet type housing to contain the measurement unit, the power source unit, and the cable (i.e., construction 1-3).

Moreover, with respect to the pulse wave sensor in accordance with the construction 1-3, the measurement unit includes a light sensor to detect an intensity of the light emitted to the wrist and penetrates a living body (i.e., construction 1-4).

Moreover, with respect to the pulse wave sensor in accordance with the construction 1-4, wherein an output wavelength of the light sensor belongs to the visible light region and is smaller than or equal to 600 nm approximately (i.e., construction 1-5).

Moreover, the pulse wave sensor in accordance with the construction 1-4 or 1-5 includes a display unit provided at the armlet type housing to provide display information (i.e., construction 1-6).

Moreover, with respect to the pulse wave sensor in accordance with the construction 1-6, wherein the measurement unit is provided at backside of the display unit (i.e., construction 1-7).

Moreover, with respect to the pulse wave sensor in accordance with the construction 1-6, wherein the multiple measurement units are provided and located to circumferential direction of the armlet type housing and each of the multiple units is facing to the display unit (i.e., construction 1-8).

Moreover, with respect to the pulse wave sensor in accordance with the construction 1-8, wherein the multiple measurement units are located as the angle of respective two lines connecting between two units located at both ends of the measurement unit row and shaft center of the armlet type housing becomes sixty to ninety degrees (i.e., construction 1-8).

Moreover, the pulse wave sensor in accordance with the construction 1-9 includes a controller to perform ON/OFF control of each of the multiple measurement units (i.e., construction 1-10).

Moreover, with respect to the pulse wave sensor in accordance with the construction 1-10, wherein the controller switches a first operation mode to turn OFF the measurement unit located around the center of the measurement unit row and to turn ON the measurement unit located around both ends of the measurement unit row and a second operation mode to turn ON the measurement unit located around the center of the measurement unit row and to turn OFF the measurement unit located around both ends of the unit row (i.e., construction 1-11).

Moreover, with respect to the pulse wave sensor in accordance with the construction 1-11, wherein the controller performs a display direction control of the display unit in conjunction with the ON/OFF control of each of the multiple measurement units (i.e., construction 1-12).

Moreover, with respect to the pulse wave sensor in accordance with the construction 1-4 or 1-5, wherein the multiple measurement units are located equally spaced from one another around the armlet type housing (i.e., construction 1-13).

Moreover, with respect to the pulse wave sensor in accordance with the construction 1-13, wherein the number of the power source units is smaller than that of the multiple measurement units and power is supplied from a single power unit to multiple measurement units (i.e., construction 1-14).

Moreover, with respect to the pulse wave sensor in accordance with the construction 1-13, wherein same number of the power source units is provided as the multiple measurement units, and power is supplied from a single power unit to a single measurement unit (i.e., construction 1-15).

Moreover, with respect to the pulse wave sensor in accordance with the construction 1-4 to 1-15, wherein the measurement unit includes an amplifier circuit to amplify an output signal of the light sensor, and a processing circuit to acquire information related to the pulse wave based on the output signal of the amplifier circuit (i.e., construction 1-16).

Moreover, with respect to the pulse wave sensor in accordance with the construction 1-16, wherein the measurement unit comprises a substrate having a surface on which the light sensor is mounted and having a rear face on which the amplifier circuit and the processing circuit are mounted. (i.e., construction 1-17).

Moreover, with respect to the pulse wave sensor in accordance with the construction 1-3 to 1-17, wherein the power source unit includes a battery, and a power source circuit to convert an input voltage from the battery to an intended output voltage (i.e., construction 1-18).

Moreover, with respect to the pulse wave sensor in accordance with the construction 1-18, wherein the power source unit includes a charge circuit to perform charge control of the battery (i.e., construction 1-19).

Moreover, with respect to the pulse wave sensor in accordance with the construction 1-19, wherein the charge circuit receives a power supply from outside by a contact method (i.e., construction 1-20).

Moreover, with respect to the pulse wave sensor in accordance with the construction 1-19, wherein the charge circuit receives a power supply from outside by a non-contact method (i.e., construction 1-21).

Moreover, the pulse wave sensor in accordance with the construction 1-3 to 1-21 includes a communication unit to transfer the measurement data acquired by the measurement unit to the outside (i.e., construction 1-22).

Moreover, with respect to the pulse wave sensor in accordance with the construction 1-22, wherein the communication unit includes a memory to store the measurement data, and a wireless communication circuit to transmit the measurement data wirelessly to the outside (i.e., construction 1-23).

Moreover, with respect to the pulse wave sensor in accordance with the construction 1-3 to 1-23, wherein the armlet type housing is a water-proof construction (i.e., construction 1-24).

Moreover, with respect to the pulse wave sensor in accordance with the construction 1-3 to 1-24, wherein the armlet type housing is made of an elastic element (i.e., construction 1-25).

Moreover, the pulse wave sensor disclosed in this specification includes multiple light sensor portions to detect an intensity of the light emitted to a wrist and penetrates a living body, a controller to perform ON/OFF control of each of the multiple light sensor portions, and an armlet type housing to contain the multiple light sensor portions and the controller (i.e., construction 2-1).

Moreover, with respect to the pulse wave sensor in accordance with the construction 2-1, wherein the multiple light sensor portions are located equally spaced from one another and to go round the armlet type housing (i.e., construction 2-2).

Moreover, with respect to the pulse wave sensor in accordance with the construction 2-1 or 2-2, wherein the controller turns OFF the multiple light sensor portions with output shortage (i.e., construction 2-3).

Moreover, with respect to the pulse wave sensor in accordance with the construction 2-1 to 2-3, wherein the controller turns OFF the multiple light sensor portions with frequency abnormality (i.e., construction 2-4).

Moreover, the pulse wave sensor in accordance with the construction 2-1 to 2-4 includes an acceleration sensor portion, wherein the controller performs ON/OFF control of each of the multiple light sensor portions according to an output of the acceleration sensor portion (i.e., construction 2-5).

Moreover, the pulse wave sensor disclosed in this specification includes multiple light sensor portions to detect an intensity of the light emitted to an wrist and penetrates a living body, a controller to perform an addition or a subtraction for each output of the multiple light sensor portions, and an armlet type housing to contain the multiple light sensor portions and the controller (i.e., construction 2-6).

Moreover, with respect to the pulse wave sensor in accordance with the construction 2-1 to 2-6, a power source portion to supply power to the multiple light sensor portions and the controller (i.e., construction 2-7).

Moreover, the pulse wave sensor in accordance with the construction 2-1 to 2-7 includes a communication portion to transfer the measurement data acquired by the multiple light sensor portions to the outside (i.e., construction 2-8).

Moreover, with respect to the pulse wave sensor in accordance with the construction 2-1 to 2-8, wherein output wavelengths of the multiple light sensor portions belong to the visible light region and are smaller than or equal to 600 nm approximately (i.e., construction 2-9).

Moreover, with respect to the pulse wave sensor in accordance with the construction 2-1 to 2-9, wherein the armlet type housing is a water-proof construction (i.e., construction 2-10).

Moreover, with respect to the pulse wave sensor in accordance with the construction 2-1 to 2-10, wherein the armlet type housing is made of an elastic element (i.e., construction 2-11).

Moreover, the pulse wave sensor disclosed in this specification includes a first light emitting portion to emit light of a first emission intensity to a living body, and a first light receiving portion to receive returned light emitted from the first light emitting portion and penetrates the living body and to generate a first light receiving signal. The pulse wave sensor further includes a second light sensor including, a second light emitting portion to emit light of a second emission intensity weaker than the first emission intensity to the living body, and a second light receiving portion to receive returned light emitted from the second light emitting portion and penetrates the living body and to generate a second light receiving signal, and a processing circuit to acquire the pulse wave data based on a subtraction of the second light receiving signal from the first light receiving signal (i.e., construction 3-1).

Moreover, with respect to the pulse wave sensor in accordance with the construction 3-1, wherein the first light sensor and the second light sensor are located adjacent to each other (i.e., construction 3-2).

Moreover, with respect to the pulse wave sensor in accordance with the construction 3-2, wherein the first light emitting portion and the second light receiving portion are located to keep a distance each other, and the second light emitting portion and the first light receiving portion are located to keep a distance each other (i.e., construction 3-3).

Moreover, with respect to the pulse wave sensor in accordance with the construction 3-1 to 3-3, wherein the processing circuit comprises a differential amplifier to output a difference signal between the first light receiving signal and the second light receiving signal (i.e., construction 3-4).

Moreover, with respect to the pulse wave sensor in accordance with the construction 3-4, wherein the processing circuit comprises a high-pass filter to cut off a low frequency component superimposed on the difference signal (i.e., construction 3-5).

Moreover, with respect to the pulse wave sensor in accordance with the construction 3-4 to 3-5, wherein the processing circuit comprises a low-pass filter to cut off a high frequency component superimposed on the difference signal (i.e., construction 3-6).

Moreover, with respect to the pulse wave sensor in accordance with the construction 3-4 to 3-6, wherein the processing circuit comprises an amplifier to amplify the differential signal (i.e., construction 3-7).

Moreover, with respect to the pulse wave sensor in accordance with the construction 3-4 to 3-7, wherein the processing circuit comprises a front stage amplifier to amplify the second light receiving signal and to provide the amplified signal to the differential amplifier (i.e., construction 3-8).

Moreover, the pulse wave sensor in accordance with the construction 3-1 to 3-8 includes a light shielding member to cover the first light sensor and the second light sensor (i.e., construction 3-9).

Moreover, with respect to the pulse wave sensor in accordance with the construction 3-9, wherein the light shielding member is a finger bag type housing (i.e., construction 3-10).

Moreover, with respect to the pulse wave sensor in accordance with the construction 3-9, wherein the light shielding member is a finger ring type housing (i.e., construction 3-11).

Moreover, with respect to the pulse wave sensor in accordance with the construction 3-9, wherein the light shielding member is an armlet type housing (i.e., construction 3-12).

Moreover, with respect to the pulse wave sensor in accordance with the construction 3-9, wherein the light shielding member is a mask type housing (i.e., construction 3-13).

Moreover, the pulse wave sensor in accordance with the construction 3-1 to 3-13 includes a power source portion to supply power to each part of the pulse wave sensor (i.e., construction 3-14).

Moreover, with respect to the pulse wave sensor in accordance with the construction 3-14, wherein the power source portion comprises a battery. (i.e., construction 3-15).

Moreover, with respect to the pulse wave sensor in accordance with the construction 3-15, wherein the power source portion comprises a voltage conversion circuit to convert an input voltage from the battery to an intended output voltage (i.e., construction 3-16).

Moreover, with respect to the pulse wave sensor in accordance with the construction 3-15 to 3-16, wherein the power source portion comprises a charge circuit to perform charge control of the battery (i.e., construction 3-17).

Moreover, the pulse wave sensor in accordance with the construction 3-1 to 3-17 includes a memory to store the pulse wave data (i.e., construction 3-18).

Moreover, the pulse wave sensor in accordance with the construction 3-1 to 3-18 includes a communication portion to transmit the pulse wave data to outside of the pulse wave sensor (i.e., construction 3-19).

Other features of the invention, elements, steps, advantages, and characteristics will be apparent from the following description of the best mode and the drawings and the claims related to the description.

DETAILED DESCRIPTION OF PREFERRED EMBODIMENTS

A Principle for the Pulse Wave Measurement

Figure 1:
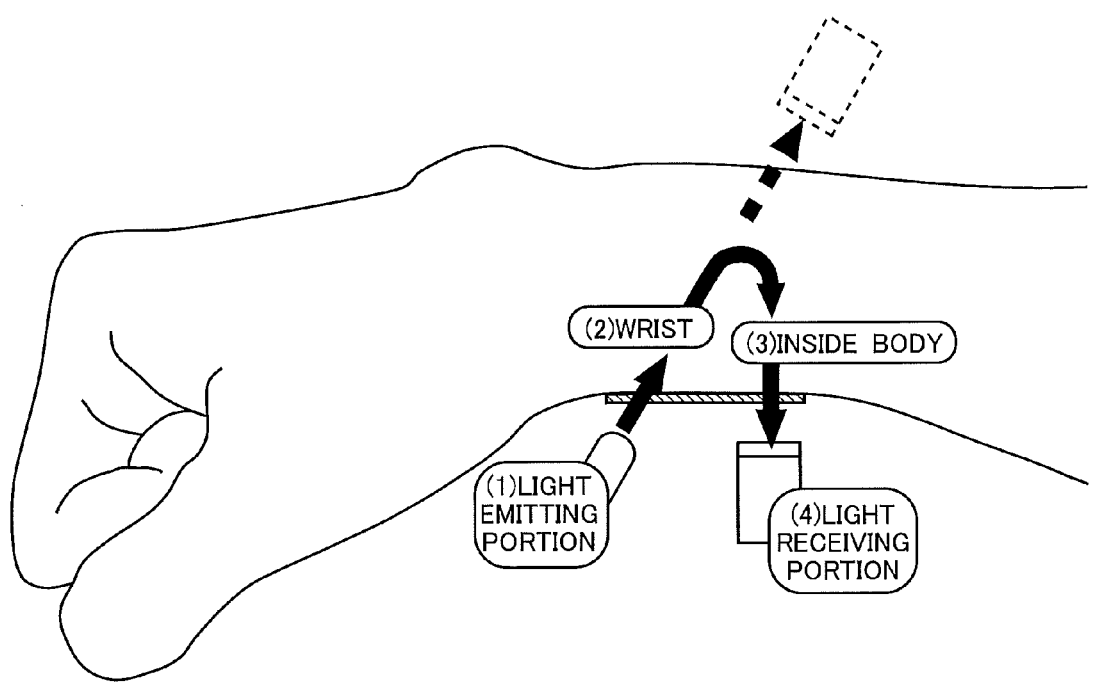
FIG. 1 is a schematic diagram to explain a principle of a pulse wave measurement in accordance with the implementation example 1 of the invention.
Figure 2:
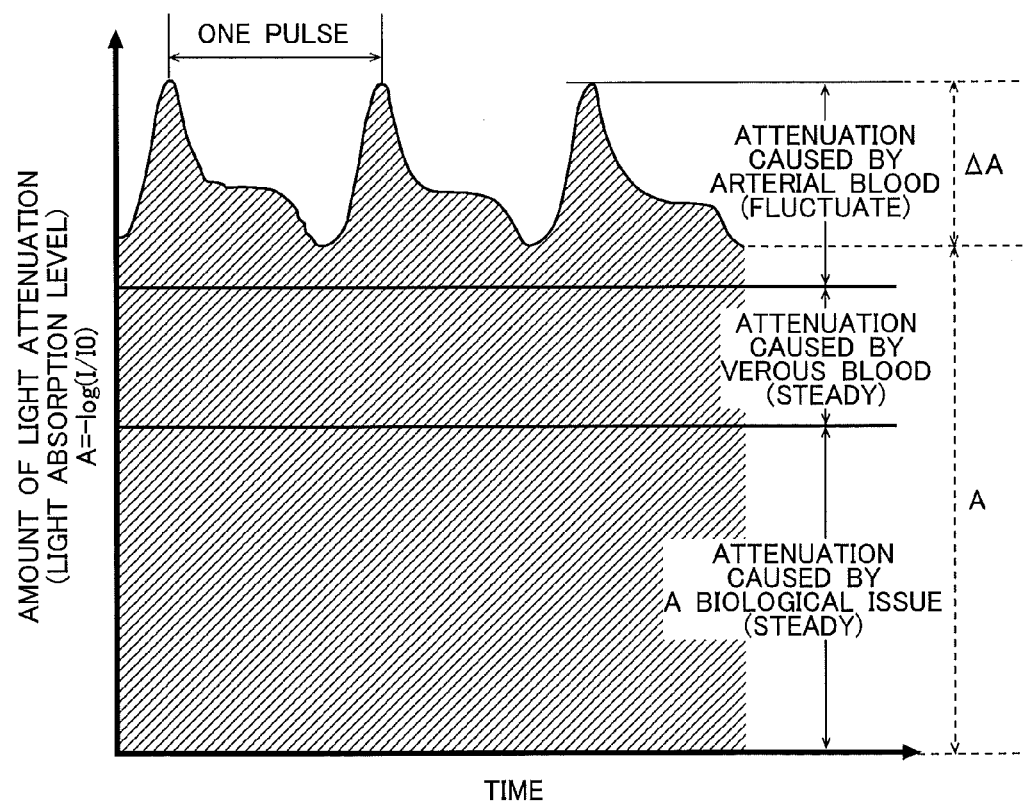
FIG. 2 is a wave form diagram illustrating a situation where the amount of light attenuation within a living body (i.e., light absorption level) changes according to the time lapse illustrated in the pulse wave measurement in FIG. 1.

FIG. 1 is a schematic diagram to explain a principle of a pulse wave measurement in accordance with the implementation example 1 of the invention. FIG. 2 is a wave form diagram illustrating a situation where the amount of light attenuation within a living body (i.e., light absorption level) changes according to the time lapse illustrated in the pulse wave measurement in FIG. 1.

For example, with respect to a pulse measurement by means of plethysmography, as illustrated in FIG. 1, the light is emitted from the light emitting portion (e.g., LED [light Emitting Diode], etc) to part of the living body (i.e., other portions work well, the wrist shown in FIG. 1 or the fingertip illustrated in FIG. 24, for example) pressed to the measurement window. Then an intensity of the light which penetrates through the body and go out of the body is detected at the light receiving portion (e.g., a photo diode or a photo transistor). Here, as illustrated in FIG. 2, although the amount of light attenuation (i.e., the light absorption level) absorbed in biological tissue or venous blood (i.e., deoxyhemoglobin Hb) is constant, the amount of light attenuation (i.e., light absorption level) absorbed by the arterial blood (i.e., oxyhemoglobin $HbO_2$) fluctuates based on the person's beat (i.e., pulse) according to the time lapse. Therefore, by using the living body window (i.e., a wave length region where the light is easy to penetrate the living body), a transition of the absorption level of the peripheral arterial can be measured and plethysmogram can be measured.

<What is Learned from the Pulse Wave>

In addition, the pulse wave controlled by a heart or autonomic nerves does not always show a constant behavior, the pulse wave gives birth the changes (i.e., fluctuations) differently based on a state of the measured person. Accordingly, based on an analysis of the pulse wave of the changes (i.e., fluctuations), various body information of the measured person can be acquired. For example, an athletic ability or tension of the measured person can be learned from the heart rate. A fatigue level, a pleasant sleep level, and a stress level of the measured person can be learned from the fluctuation of the heart rate. Furthermore, based on an acceleration pulse wave acquired by differentiating the pulse wave two times by the time axis, the blood vessel age or arterial stiffness of the measured person can be learned.

<A First Implementation>

Figure 3:
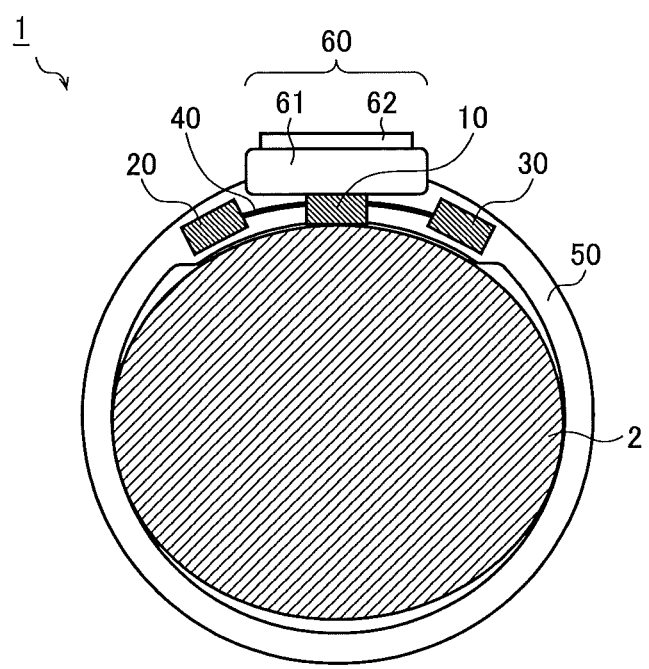
FIG. 3 is a cross section diagram illustrating a first implementation of the pulse wave sensor schematically in accordance with the implementation example 1.

FIG. 3 is a cross section diagram illustrating a first implementation of the pulse wave sensor schematically in accordance with the implementation example 1. The pulse wave sensor 1 of the first implementation has a construction to measure the pulse wave at the wrist 2, to be more concrete, which has an armlet construction (i.e., a wrist watch construction in the first implementation) to measure the pulse wave to be worn on the wrist 2. In addition, with respect to the construction elements, the pulse wave sensor 1 of the first implementation includes a measurement unit 10, a power source unit 20, a communication unit 30, a cable 40, an armlet type housing 50, and a display unit 60.

The measurement unit 10 is a unit to measure the pulse wave mainly, which is contained within the armlet type housing 50 to be located at the back side of the display unit 60. Owing to this construction, in a situation where the examinee turns the face to the display unit 60 to watch information (e.g., a result of the pulse wave measurement) displayed at the display unit 60, the measurement unit 10 is pressed to the wrist 2 according to the weight of the display unit 60, the pulse wave can be measured stably, furthermore, the accuracy for measuring the pulse wave can be improved. Moreover, with respect to the pulse wave measurement at the wrist, the inventors of this application confirmed it is possible to measure the pulse wave sufficiently, though the sensitivity is lower compared to the pulse wave measurement at the fingertip. In addition, the internal construction and the operation of the measurement unit 10 are explained in detail later.

The power source unit 20 is a unit to supply power to the measurement unit 10 and the communication unit 30 mainly, the power source unit 20 is contained within the armlet type housing 50 to be located to the back side of the wrist 2 when the armlet type 50 is worn on the wrist 2. In this way, by means of locating the second unit 20 which can be a noise source for the first unit 10 separately from the first unit 10 as an another unit, the measurement accuracy of the pulse wave can be improved. In addition, an internal construction and an operation of the power source unit 20 is explained in detail later.

The communication unit 30 is a unit to transfer the measurement data acquired at the measurement unit 10 to the outside mainly, the communication unit 30 is contained within the armlet type housing 50 to be located to the back side of the wrist 2 when the armlet type 50 is worn on the wrist 2. In this way, by means of locating the communication unit 30 which can be a noise source for the first unit 10 separately from the first unit 10 as an another unit, the measurement accuracy of the pulse wave can be improved. In addition, an internal construction and an operation of the communication unit 30 are explained in detail later.

The cable 40 is contained within the armlet type housing 50 to connect between the measurement unit 10, the power source unit 20, and the communication unit 30 each other electrically. In addition, as the cable 40, including a commonly used covered conductor, FPC [Flexible Printed Circuits] and so on can be used appropriately.

The armlet type housing 50 contains the measurement unit 10, the power source unit 20, the communication unit 30, and the cable 40. The armlet type housing 50 is worn on the wrist.

The display unit 60 is a unit to provide display information (e.g., information related to date or time, including the measurement result of the pulse wave, and so on) to be provided at the armlet type housing 50, including a main body portion 61 and a display portion 62. The main body portion 61 includes a microcomputer or a battery to control the display portion 62, and the display portion 62 includes a liquid crystal display panel, and so on. In other words, the display unit 60 is equivalent to an hour plate of the wrist watch.

As mentioned above, with respect to the pulse wave sensor 1 of the armlet construction, as long as the examinee does not take off the pulse wave sensor 1 from the wrist 2 intentionally, because there is hardly any possibility to drop the pulse wave sensor 1 from the wrist 2 when measuring the pulse wave, to measure the pulse wave without restricting the behavior of the examinee can be realized.

Moreover, with respect to the pulse wave sensor 1 of the armlet construction, the consciousness of wearing the pulse wave sensor 1 can be reduced for the examinee, even in the case of the continuous pulse wave measurement for a long period (i.e., few days to few months), excess stress can be avoided for the examinee.

Especially, with respect to the first implementation which the display unit 60 is provided at the armlet type housing 50, because the pulse wave sensor 1 can be worn as wrist watch on a daily basis, resistance feeling against wearing the pulse wave sensor 1 can be eliminated, furthermore, a contribution to develop new users can be realized.

In addition, forming the armlet type housing 50 with elastic elements (e.g., silicon rubber) makes it possible to provide flexibility for the possible size to wear the pulse wave sensor 1.

Moreover, it is desirable to design the armlet type housing 50 and the display unit 60 as water-proof construction. This construction makes it possible to measure the pulse wave without breaking down even if it is soaked to water (e.g., rain) or sweat. Furthermore, if the pulse wave sensor 1 is shared by many persons (e.g., when used as rental at sports gym), as the armlet type housing 50 can be washed just as it is, and the pulse wave sensor 1 can be kept clean.

Moreover, with respect to the first implementation, although an explanation is described in reference to a construction which all of the measurement unit 10, the power source unit 20, the communication unit 30, and the display unit 60 are independent from one another, a construction of the invention is not restricted to this, multiple units can be integrated to one unit.

<A Measurement Unit>

Figure 4:
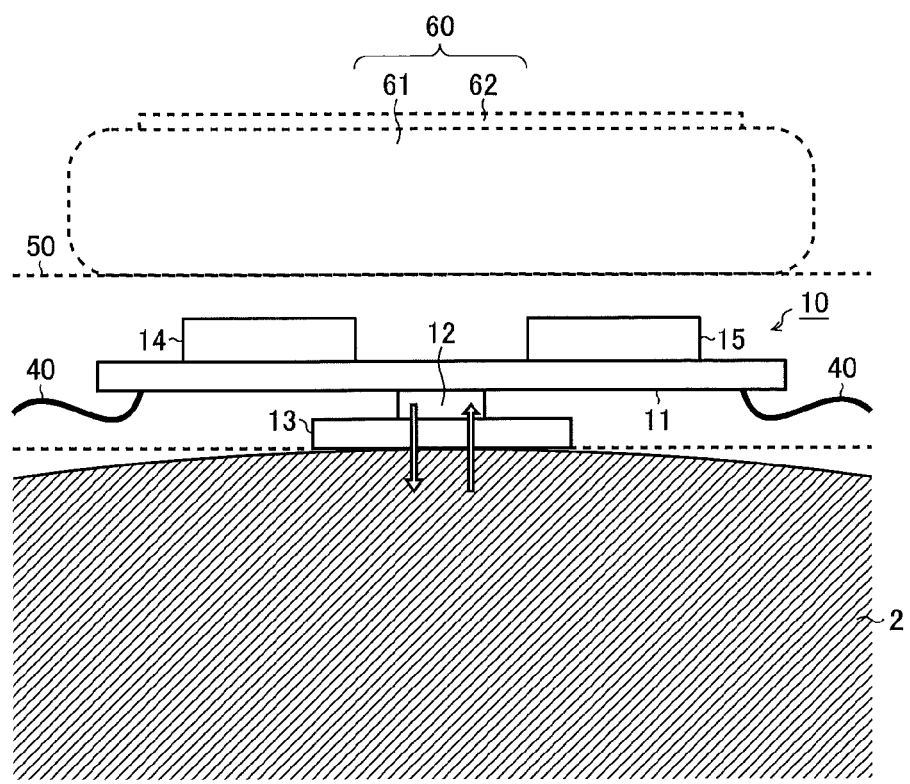
FIG. 4 is a cross section diagram illustrating a construction example of the measurement unit 10 schematically.

FIG. 4 is a cross section diagram illustrating a construction example of the measurement unit 10 schematically. The measurement unit 10 of this construction example includes a substrate 11, a light sensor 12, a measurement window 13, an amplifier circuit 14, and the processing circuit 15.

The light sensor 12 is mounted to the surface of the substrate 11 directly, the amplifier circuit 14 and the processing circuit 15 are mounted to the back side of the substrate 11 directly. Moreover, the cable 40 to establish an electrical connection with the power source unit 20 and the communication unit 30 are connected to the substrate 11. In addition, the electrical connection is established between the surface and back side of the substrate 11 by means of a through hole and a via hole. In this way, with respect to a construction to directly mount the light sensor 12, the amplifier circuit 14, and the processing circuit 15, then the measurement unit 10 can be designed as thin, the wear feeling of the pulse wave sensor 1 can be improved. Furthermore, with respect to the construction to mount only the light sensor 12 to the surface of the substrate 11, the light sensor 12 can be located at the vicinity of the wrist 2 as much as possible, then the measurement accuracy of the pulse wave can be improved.

By emitting the light from the light emitting portion to the wrist 2 and detect the intensity of the light which penetrates the living body by the light receiving portion, the light sensor 12 acquires the pulse wave data. In addition, the light sensor 12 in accordance with this construction example is not a construction both the light emitting portion and the light receiving portion are provided at opposite side against the wrist 2 each other (i.e., a so-called penetration type, in reference to a broken line arrow in FIG. 1). The light sensor 12 is a construction both the light emitting portion and the light receiving portion are provided at same side against the wrist 2 (i.e., a so-called reflection type, in reference to a full line arrow in FIG. 1).

The measurement window 13 is constructed with the translucency member (i.e., a glass plate or an acrylic plate, and so on) which is provided at the light emitting/receiving surface of the light sensor 12. The light sensor 12 performs the measurement of the pulse wave (i.e., detection for the emitted light to the wrist 2 and a reflected light go back from the wrist 2) via this measurement window 13. In addition, with respect to the thickness of the measurement window 13, it is desirable to design appropriately in view of the depth of focus of the light sensor 12.

The amplifier circuit 14 amplifies the output signal (i.e., a detection signal of the light receiving portion) of the light sensor 12 and provides it to the processing circuit 15. In this way, with respect to a construction to equip the amplifier circuit 14 to the vicinity of the light sensor 12, the output signal of the light sensor 12 can be amplified before the noise is superimposed, then it makes possible to improve S/N [Signal/Noise Ratio] of the signal, furthermore, the measurement accuracy of the pulse wave can be improved.

The processing circuit 15 controls entire operation of the pulse wave sensor 1 generally, and also by means of performing a various signal process for the output signal of the amplifier circuit 14, it acquires various information about the pulse wave (i.e., the fluctuation of the pulse wave, the heart rate, the fluctuation of the heart rate, and the acceleration pulse wave). In addition, as the processing circuit 15, the CPU [Central Processing Unit] can be used appropriately. In this way, with respect to the construction both the light sensor 12 and the amplifier circuit 14 are located at the vicinity of the processing circuit 15, the output signal of the amplifier circuit 14 can be processed before the noise superimposes, therefore, it is possible to improve the analysis accuracy of the pulse wave.

<A Power Source Unit>

Figure 5:
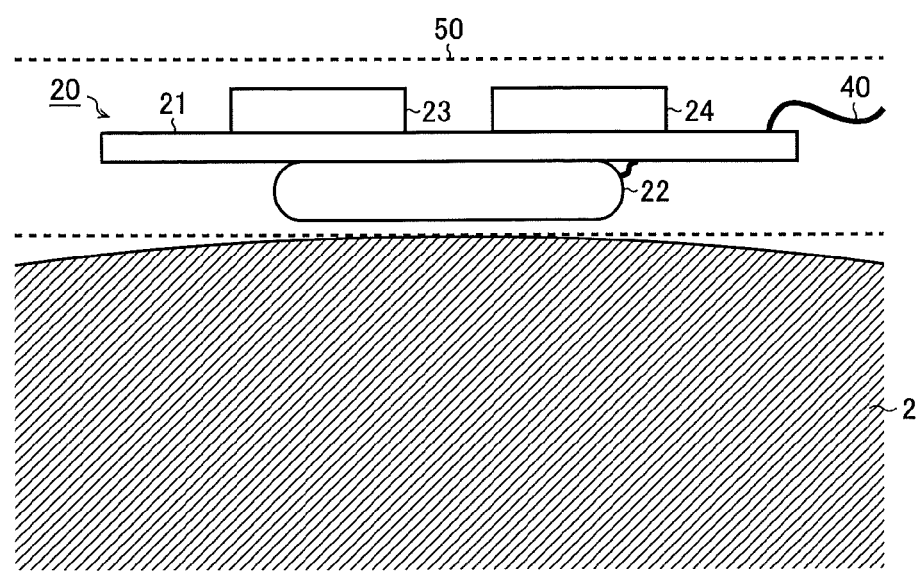
FIG. 5 is a cross section diagram illustrating a construction example of the power source unit 20 schematically.

FIG. 5 is a cross section diagram illustrating a construction example of the power source unit 20 schematically. The power source unit 20 of this construction example includes the substrate 21, the battery 22, the power source circuit 23, and the charge circuit 24.

The battery 22 is mounted to the surface of the substrate 21 directly, and the power source circuit 23 and the charge circuit 24 are mounted to the back side of the substrate 21 directly. Moreover, the cable 40 to establish the electrical connection with the measurement unit 10 is connected to the substrate 21. In addition, the electrical connection is established between the surface and back side of the substrate 21 by means of the through hole and the via hole. In this way, by means of utilizing both sides of the substrate 21 efficiently, the area of the substrate 21 can be reduced. Therefore, the power source unit 20 can be miniaturized. Furthermore, a consciousness of the examinee for wearing the pulse wave sensor 1 can be reduced.

The battery 22 is a power supply source required to drive the pulse wave sensor 1, a lithium ion secondary battery or an electrical double layer capacitor can be used appropriately. In this way, with respect to the pulse wave sensor 1 of battery drive type, there is no need to connect a power supply cable from outside during the measurement of the pulse wave. Measurement of the pulse wave can be realized without restricting the behavior of the examinee. In addition, according to this construction, the battery 22 formed as highly flat is located right above the wrist 2, it is possible to improve an affinity of the pulse wave sensor 1 when the pulse sensor 1 is worn on the wrist 2, furthermore, the consciousness of the examinee for wearing the pulse wave sensor 1 can be reduced.

The power source circuit 23 converts the input voltage from the battery 22 to an intended output voltage and supply it to each part of the pulse wave sensor 1. In this way, by means of embedding the power source circuit 23 which can be a noise source for the measurement unit 10 to the power source unit 20 which is independent from the measurement unit 10, the measurement accuracy of the pulse wave can be improved.

The charge circuit 24 performs the charge control of the battery 22 based on the power source supply from outside. In addition, as the power supply methods from outside, a contact method as using the USB [Universal Serial Bus] cable, or a non-contact method as an electromagnetic induction method, an electric field connection method, or an electric field resonance method can be used. Owing to a construction having a charge method for the battery 22, a battery swapping operation is not required, utility of the pulse wave sensor 1 can be improved. In addition, for designing the armlet type housing 50 as the water-proof construction, in terms of eliminating external terminals completely, it is desirable to adopt non-contact method as a method to supply power to the charge circuit 24.

<A Communication Unit>

Figure 6:
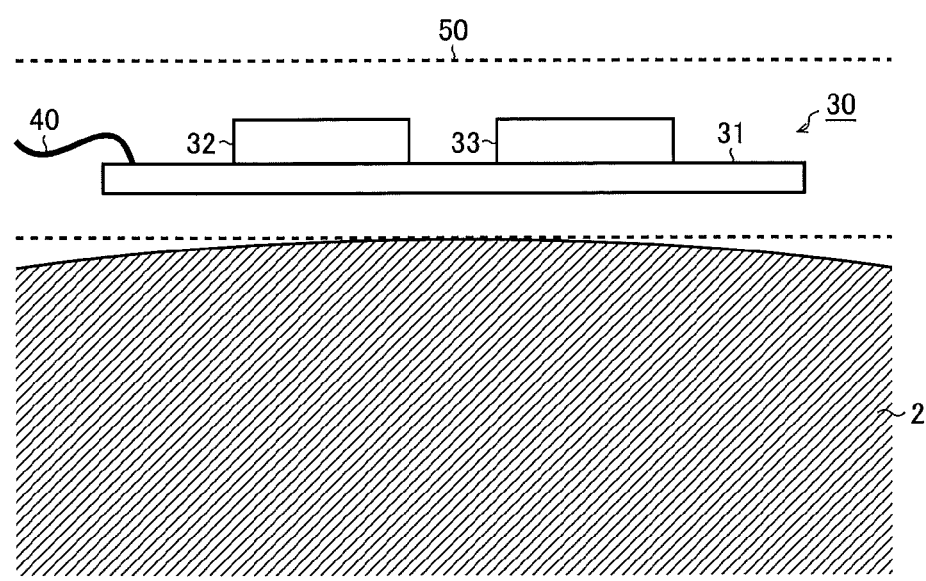
FIG. 6 is a cross section diagram illustrating a construction example of the communication unit 30 schematically.

FIG. 6 is a cross section diagram illustrating a construction example of the communication unit 30 schematically. The communication unit 30 of this construction includes the substrate 31, the memory 32, and the wireless communication circuit 33.

Both the memory 32 and the wireless communication circuit 33 are mounted to the surface of the substrate 31 directly. Moreover, the cable 40 to establish the electrical connection between the measurement unit 10 is connected to the substrate 31.

The memory 32 stores the measurement data acquired at the measurement unit 10 (i.e., a raw data provided from the amplifier circuit 14 or a processed data various processes are performed at the processing circuit 15) as volatile or non-volatile method. In addition, as the memory 32, a volatile RAM [Random Access Memory] or a non-volatile flash memory can be used appropriately. With respect to a construction which has a storing method for the measurement data, because accumulated data of the memory 32 can be sent to outside by means of the batch transmission in every predetermined period, it is possible to let the wireless communication circuit 33 be a standby state intermittently, furthermore, the battery drive time of the pulse wave sensor 1 can be extended.

The wireless communication circuit 33 transmits the measurement data acquired at the measurement unit 10 (i.e., the raw data provided from the amplifier circuit 14, the processed data various processes has performed provided from the processing circuit 15, or the stored data provided from the memory 32) to the external personal computer or a cell phone. Because the wireless communication circuit 33 can be a noise source for the measurement unit 10 same as the power source circuit 23, it is desirable to embed the wireless communication circuit 33 to the communication unit 30 independent from the measurement unit 10. In addition, with respect to the wireless communication circuit 33, the Bluetooth (the registered trademark) module IC can be used appropriately for example. With respect to a construction having such wireless communication circuit 33, the wired connection is not required to transmit the measurement data to the external apparatus, it makes possible to perform a real time transmission for the measurement data without restricting the behavior of the examinee. In addition, for designing the armlet type housing 50 as the water-proof construction, in terms of eliminating external terminals completely, it is desirable to adopt non-contact method as a method to transmit the measurement data to the outside.

<A Second Implementation>

Figure 7:
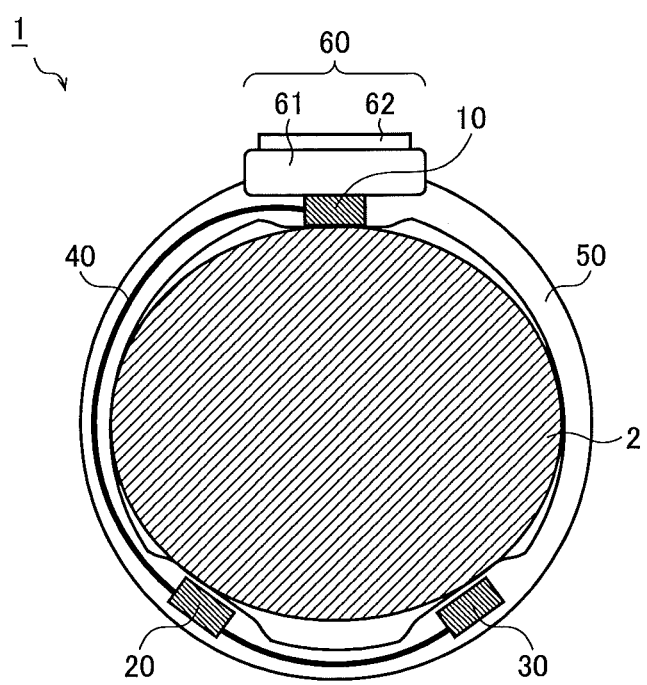
FIG. 7 is a cross section diagram illustrating a second implementation of the pulse wave sensor schematically in accordance with the implementation example 1.

FIG. 7 is a cross section diagram illustrating a second implementation of the pulse wave sensor schematically in accordance with the implementation example 1. With respect to the pulse wave sensor 1 in accordance with the second implementation, both the power source unit 20 and the communication 30 are contained to the armlet type housing 50 to be located at the inside of the wrist 2 when the armlet type housing 50 is worn on the wrist 2. In this way, by means of locating the power source unit 20 and the communication unit 30 which can be a noise source for the measurement unit 10 from the measurement unit 10 as far as possible, the measurement accuracy of the pulse wave can be improved.

<A Third Implementation>

Figure 8:
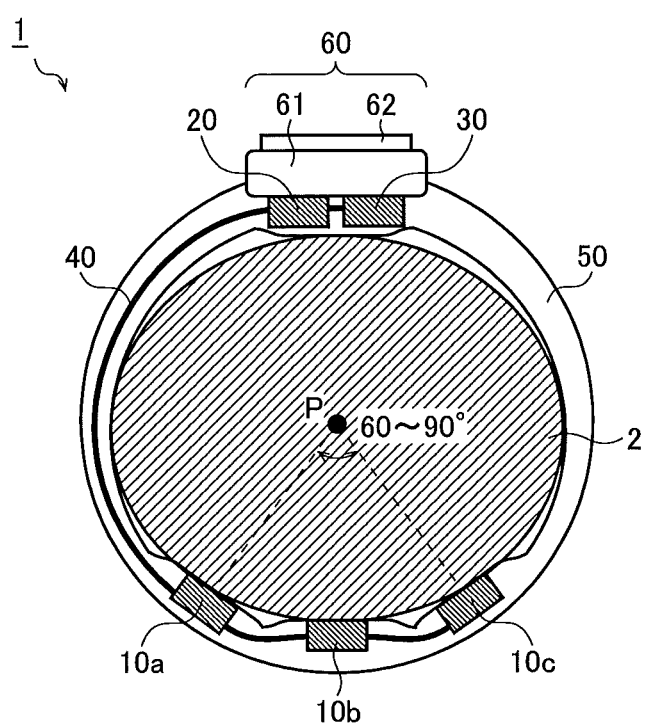
FIG. 8 is a cross section diagram illustrating a third implementation of the pulse wave sensor schematically in accordance with the implementation example 1.

FIG. 8 is a cross section diagram illustrating a third implementation of the pulse wave sensor schematically in accordance with the implementation example 1. With respect to the pulse wave sensor 1 in accordance with the third implementation, three measurement units 10a to 10c are located to circumferential of the armlet type housing 50 and each of them is facing to the display unit 60. To be more concrete, with respect to the measurement unit 10b located at the center of the measurement unit row, the measurement unit 10b is located as symmetrical about a point with the display unit 60 against the shaft center P when the armlet type housing 50 is seen from the direction of the shaft center (i.e., cross section view). With respect to both of the measurement units 10a and 10c located at both ends of the measurement unit row, the units are located as the angle of respective two lines connecting between two units and the shaft center P becomes sixty to ninety degrees. Moreover, both the power source unit 20 and the communication unit 30 are contained within the armlet type housing 50 to be located at the back side of the display unit 60.

Owing to this construction, regardless of wearing state of the pulse wave sensor 1, the pulse wave can be measured appropriately by at least one of the measurement unit 10a to 10c. The reason is explained concretely later in reference to FIG. 9 and FIG. 10.

Figure 9:
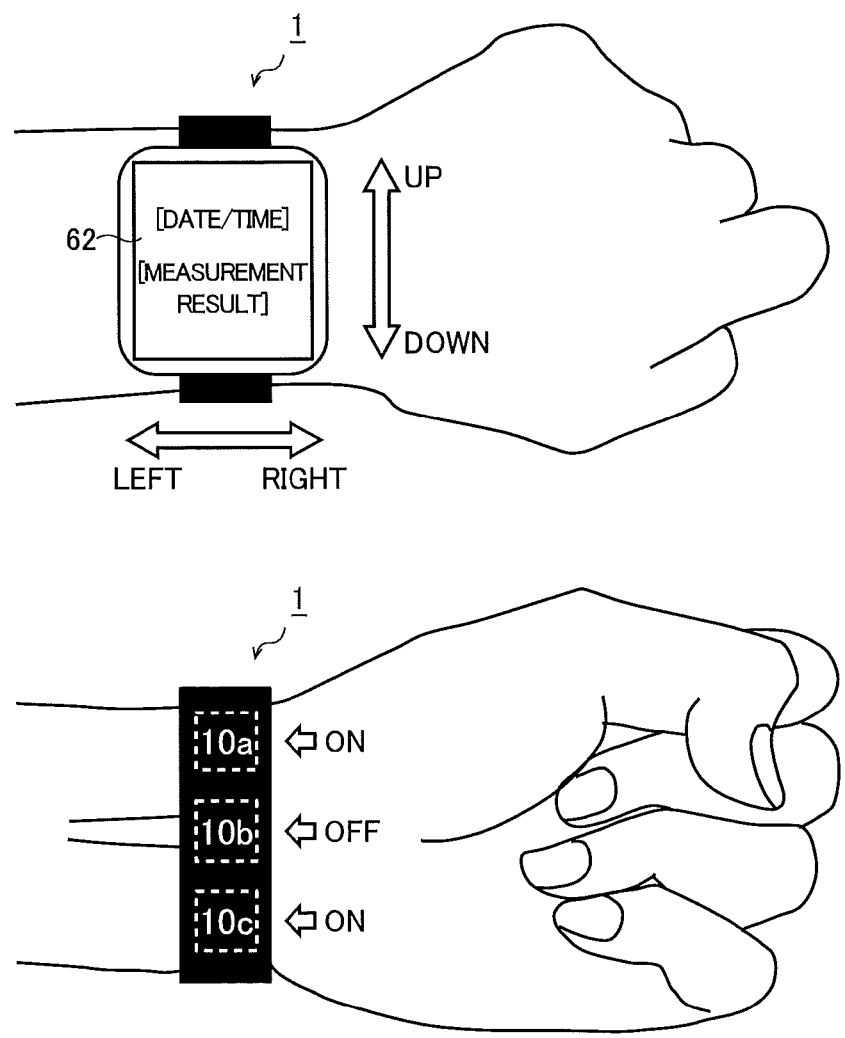
FIG. 9 is a schematic diagram to explain a first wearing state of the pulse sensor 1.
Figure 10:
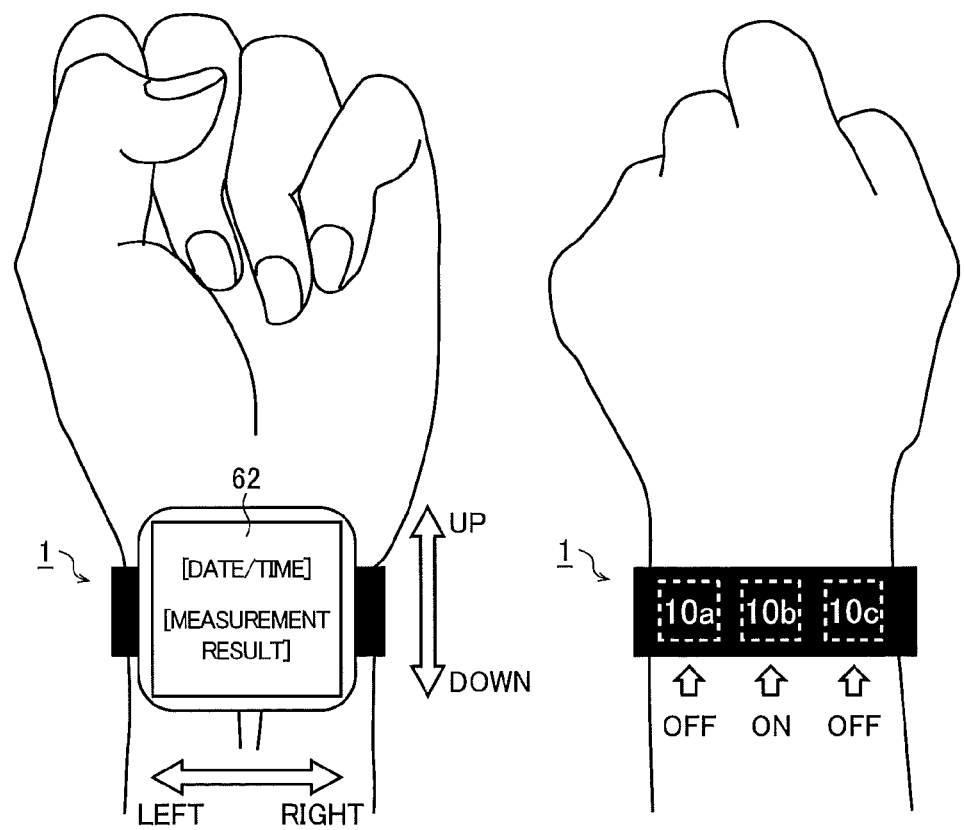
FIG. 10 is a schematic diagram to explain a second wearing state of the pulse sensor 1.

FIG. 9 is a schematic diagram to explain a first wearing state of the pulse sensor 1 (i.e., a state where the pulse wave sensor 1 is worn with the display unit 60 is located at the back side of the wrist 2). FIG. 10 is a schematic diagram to explain a second wearing state of the pulse sensor 1 (i.e., a state where the pulse wave sensor 1 is worn with the display unit 60 is located at the inside of the wrist 2).

With respect to the inside of the wrist 2, though fit feeling of the pulse wave sensor 1 around the center portion is scanty because of the tendon located right beneath the skin, fit feeling of the pulse wave sensor 1 around the both ends is fine because of the thick flesh. Accordingly, with respect to the first wearing state of the pulse wave sensor 1, the pulse wave can be measured appropriately by the measurement units 10a and 10c located at both ends of the measurement unit row.

On the other hand, with respect to the back side of the wrist 2, though fit feeling of the pulse wave sensor 1 around both ends is scanty because of the born located right beneath the skin, fit feeling of the pulse wave sensor 1 around center portion is fine because of the thick flesh. Accordingly, with respect to the second wearing state of the pulse wave sensor 1, the pulse wave can be measured appropriately by the measurement unit 10b located at the center of the measurement unit row.

As mentioned above, with respect to the first wearing state of the pulse wave sensor 1, measurement units 10a and 10c located at both ends of the measurement unit row are able to measure the pulse wave accurately than the measurement unit 10b located at the center of the measurement unit row. With respect to the second wearing state of the pulse wave sensor 2, measurement unit 10b located at the center of the measurement unit row is able to measure the pulse wave accurately than the measurement units 10a and 10c located at both ends of the measurement units.

To put it the other way around, the necessity of the operation of the measurement unit 10b is scanty with respect to the first wearing state of the pulse wave sensor 1, the necessity of the operation of the measurement unit 10a and 10c is scanty with respect to the second wearing state of the pulse wave sensor 2.

Therefore, with respect to the pulse wave sensor 1 in accordance with the third implementation, a construction to perform ON/OFF control for each of the measurement units 10a to 10c is adopted. To be more concrete, the controller switches the first operation mode which the measurement unit 10b is turned OFF and the measurement units 10b and 10a are turned ON and the second operation mode which the measurement unit 10b is turned ON and the measurement units 10a and 10c are turned OFF according to the switch control of the operation mode by examinee.

In addition, the controller can be implemented as one function of the processing circuit embedded to the measurement units 10a to 10c, or a microcontroller can be embedded to the power source unit 20, the communication unit 30, or the display unit 60. Or else, the controller can be contained as an independent unit to the armlet type housing 50 to perform general control of the measurement units 10a to 10c.

Owing to this construction, the measurement units 10a to 10c can be turned ON/OFF according to need, the power consumption can be reduced and the battery drive time can be extended.

Moreover, with respect to the pulse wave sensor 1 in accordance with the third implementation, the controller performs the display direction control of the display unit 60 in conjunction with the ON/OFF control of the measurement units 10a to 10c. To be more concrete, the display direction control is performed to synchronize the circumferential direction of the armlet type housing 50 with the vertical direction of the provided display information to the display portion 62 in the first operation mode. The display direction control is performed to synchronize the circumferential direction of the armlet type housing 50 with the horizontal direction of the provided display information to the display portion 62 in the second operation mode. Owing to this construction, regardless of the wearing state of the pulse wave sensor 1, the display information can be read easily by the examinee.

<A Fourth Implementation>

Figure 11:
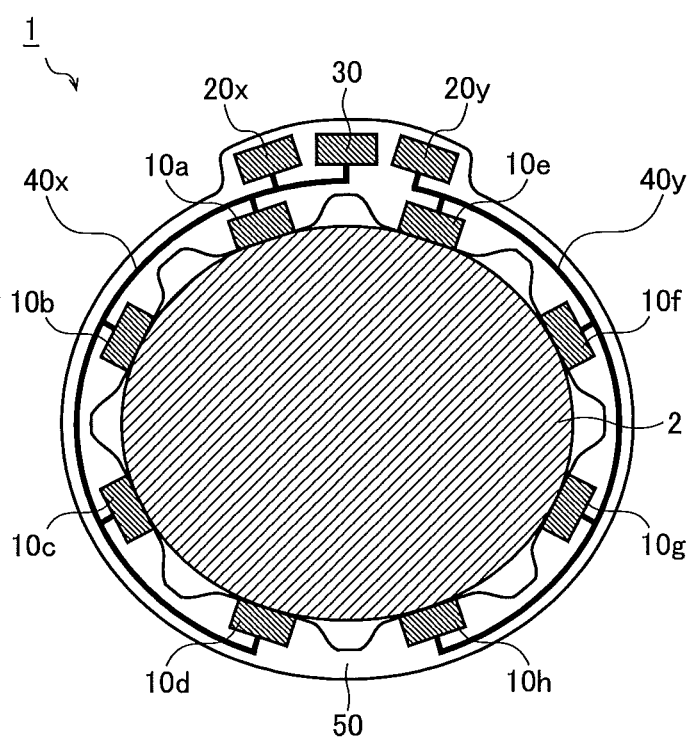
FIG. 11 is a cross section diagram illustrating a fourth implementation of the pulse wave sensor schematically in accordance with the implementation example 1.

FIG. 11 is a cross section diagram illustrating a fourth implementation of the pulse wave sensor schematically in accordance with the implementation example 1. With respect to the pulse wave sensor 1 of the fourth implementation, the display unit 60 is eliminated and eight measurement units 10a to 10h are located equally spaced from one another and to go round the armlet type housing 50. With respect to this construction, even when the armlet type housing 50 rotates around the wrist 2, the pulse wave can be measured appropriately by at least one of the measurement units 10a to 10h.

Moreover, with respect to the pulse wave sensor 1 in accordance with the fourth implementation, two power supply units 20x and 20y are provided for eight measurement units 10a to 10h, power is supplied from one power supply unit to multiple measurement units. To be more concrete, power source unit 20x supply power to the measurement units 10a to 10d and the communication unit 30 via the cable 40x, and the power source unit 20y supply power to the measurement units 10e to 10h via the cable 40y. Owing to this construction, the burden for the power source unit can be reduced. Moreover, the cable can be divided to multiple segments, it is possible to response flexibly to stretch of the armlet type housing 50.

In addition, with respect to the pulse wave sensor 1 in accordance with the fourth implementation, the power source unit 20x and 20y and the communication unit 30 are put together at one location of the armlet type housing 50 and contained.

<A Fifth Implementation>

Figure 12:
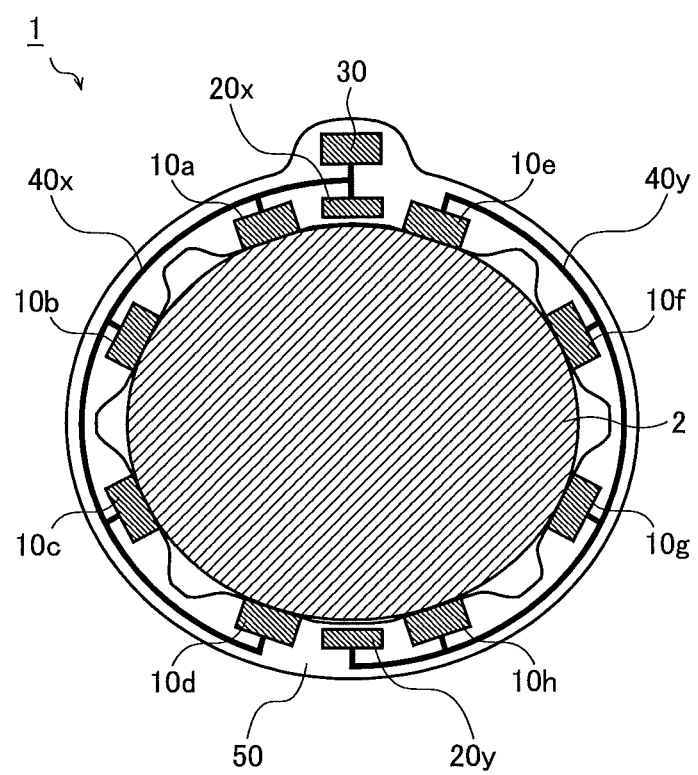
FIG. 12 is a cross section diagram illustrating a fifth implementation of the pulse wave sensor schematically in accordance with the implementation example 1.

FIG. 12 is a cross section diagram illustrating a fifth implementation of the pulse wave sensor schematically in accordance with the implementation example 1. With respect to the pulse wave sensor 1 in accordance with the fifth implementation, the power source units 20x and 20y are formed thinner and more miniaturized than the measurement units 10a to 10h. The power source unit 20x is located between the measurement unit 10a and the measurement unit 10e, and the power source unit 20y is located between the measurement unit 10d and the measurement unit 10h respectively. Owing to this construction, same as the aforementioned fourth implementation, even when the armlet type housing 50 rotates around the wrist 2, the pulse wave can be measured appropriately by at least one of the measurement units 10a to 10h.

<A Sixth Implementation>

Figure 13:
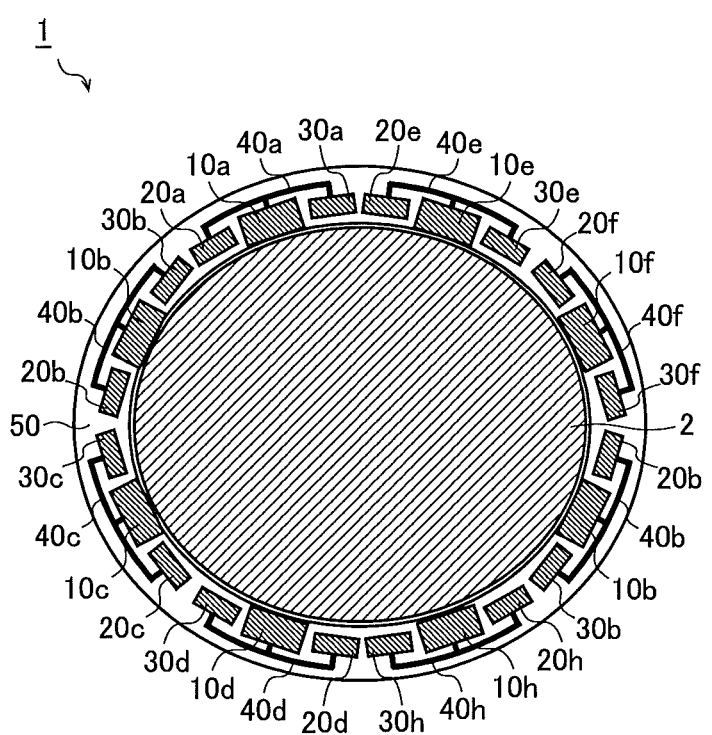
FIG. 13 is a cross section diagram illustrating a sixth implementation of the pulse wave sensor schematically in accordance with the implementation example 1.

FIG. 13 is a cross section diagram illustrating a sixth implementation of the pulse wave sensor schematically in accordance with the implementation example 1. With respect to the pulse wave sensor 1 in accordance with the sixth implementation, eight power source units 20a to 20h, eight communication units 30a to 30h, and eight cables 40a to 40h are provided for eight measurement units 10a to 10h, power is supplied to one measurement unit and one communication unit from one power source unit via one cable. In other words, the pulse wave sensor 1 in accordance with the sixth implementation is a construction which eight independent blocks are contained to armlet type housing 50, each of the independent blocks is able to measure the pulse wave independently and transmit the measurement data to the outside. Owing to this construction, same as the aforementioned fourth implementation or fifth implementation, even when the armlet type housing 50 rotates around the wrist 2, the pulse wave can be measured appropriately by at least one of the measurement units 10a to 10h.

<A Light Sensor>

Figure 14:
FIG. 14 is a cross section diagram illustrating a layout patterns A to D of a light emitting portion and a light receiving portion.
Figure 14:
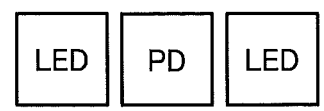
Figure 14:
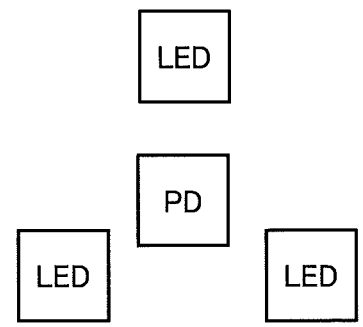
Figure 14:
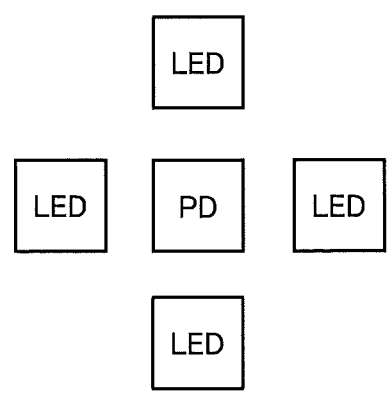
Figure 15:
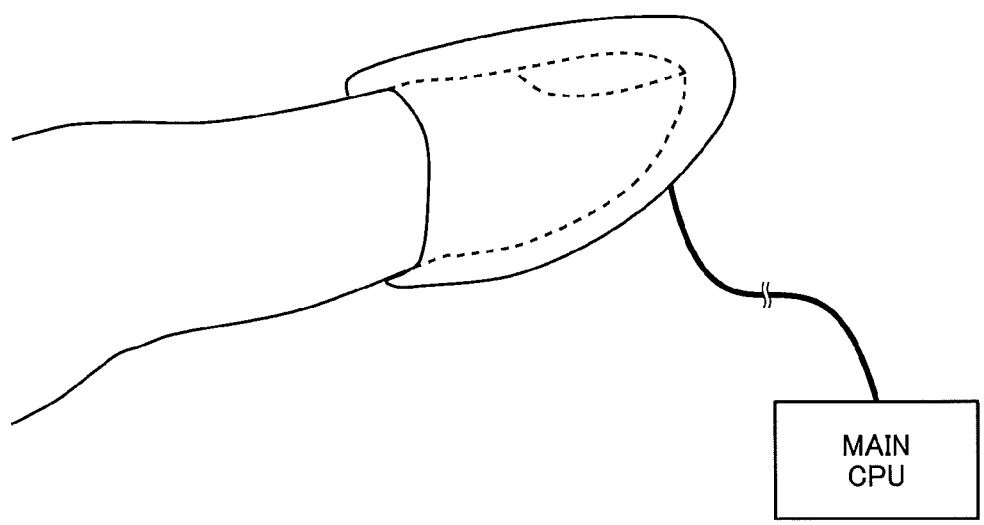
FIG. 15 is a schematic diagram illustrating a conventional example of the pulse wave sensor.

FIG. 14 is a cross section diagram illustrating a layout patterns A to D of a light emitting portion and a light receiving portion forming the light sensor 12 of the measurement unit 10. As illustrated in FIG. 14, for the light emitting portion LED and the light receiving portion PD, either layout patterns of 1 by 1 (i.e., layout patter A), 2 by 1 (i.e., layout pattern B), 3 by 1 (i.e., layout pattern C), and 4 by 1 (i.e., layout pattern D), and so on, can be adopted. In addition, in the case of adopting the layout patterns B to D, it is desirable to locate multiple light emitting portions (i.e., LED) to vertex of the regular polygon and to locate the light receiving portion to weighted center of the regular polygon.

<Consideration about the Output Wave Length>

In the experiment, by means of the pulse wave sensor 1 of so-called reflection type, each output wave length of the light emitting portions is set to $\lambda 1$ (infrared: 940 mm), $\lambda 2$ (green: 630 nm), and $\lambda 3$ (blue: 468 nm), and each behavior is examined when the output intensity of the light emitting portions (i.e., driving current value) are varied to 1 mA, 5 mA, and 10 mA. As the result, with respect to the visible light region whose wave length is shorter than or equal to 600 nm, it is examined that the wave form of the pulse wave can be acquired relatively easy because the absorption coefficient of oxyhemoglobin $HbO_2$ becomes larger and the peak intensity of the measured pulse wave becomes larger.

In addition, with respect to the pulse oxymeter to detect the oxygen saturation of the arterial blood, although the wave length of the near-infrared region (approximately 700 nm) where the difference between the absorption coefficient of the oxyhemoglobin $HbO_2$ (shown in full line) and the absorption coefficient of the deoxyhemoglobin Hb becomes maximum is used as the output wave length of the light emitting portion universally, in consideration of usage as the pulse wave sensor, as illustrated in the aforementioned experiment result, it can be determined that it is desirable to use the visible light region whose wave length is shorter than or equal to 600 nm as the output wave length of the light emitting portion.

<A Seventh Implementation>

Figure 16:
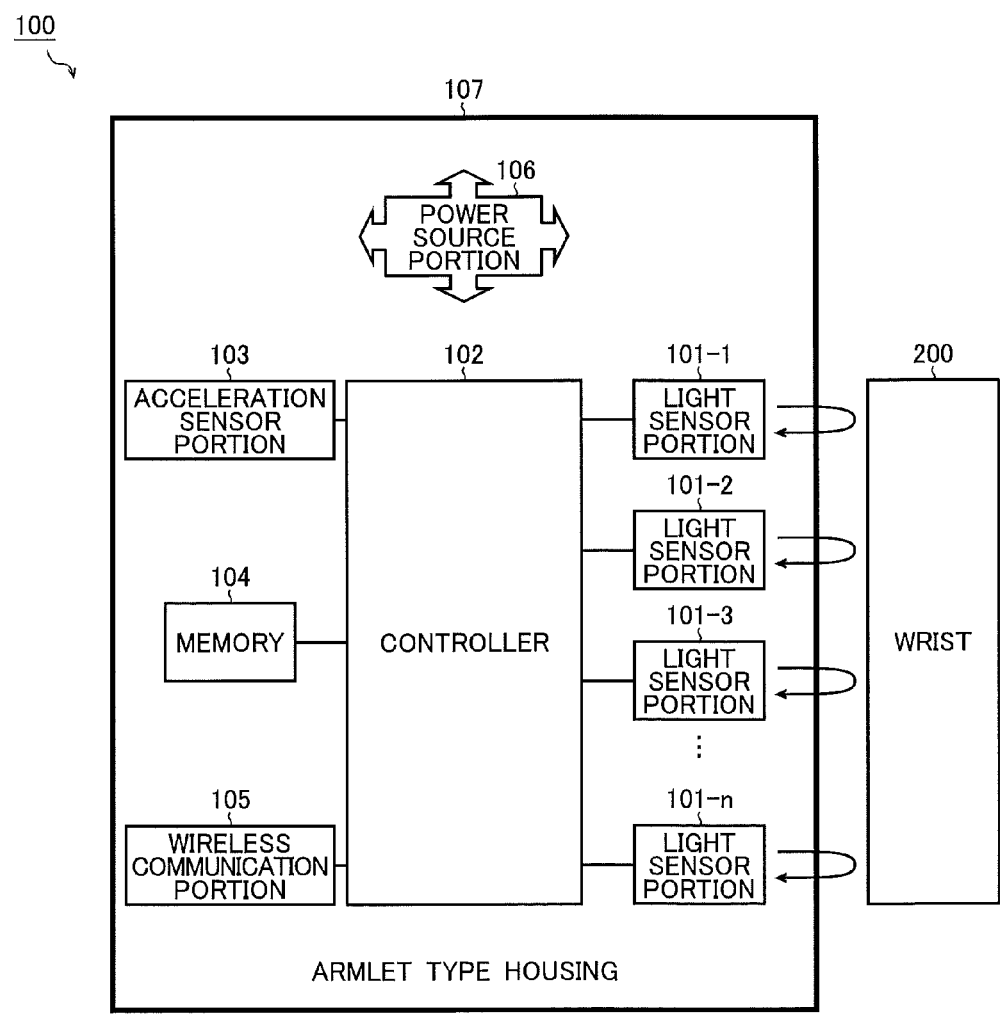
FIG. 16 is a block diagram illustrating a seventh implementation of the pulse wave sensor schematically in accordance with the implementation example 1.

FIG. 16 is a block diagram illustrating a seventh implementation of the pulse wave sensor schematically in accordance with the implementation example 1. The pulse wave sensor 100 in accordance with the seventh implementation includes n (n=larger than or equal to 2) light sensor portions 101-1 to 101-n, a controller 102, an acceleration sensor portion 103, a memory 104, a wireless communication portion 105, a power source portion 106, and an armlet type housing 107.

Each of the light sensor portions 101-1 to 101-n detects an intensity of the light emitted to the wrist 200 and penetrates a living body. The light sensor portions 101-1 to 101-n are located equally spaced from one another and to go round the armlet type housing 107 same as the fourth to sixth implementations. In addition, because the construction and the output wave length of the light sensor portions 101-1 to 101-n are same as the aforementioned light sensor 12, a redundant explanation is omitted here.

The controller 102 is equivalent to the aforementioned processing circuit 15 and control the entire operation of the pulse wave sensor 100 generally.

The acceleration sensor portion 103 detects three-axis accelerations separately and transmits to the controller 102. Owing to this construction, it is possible to recognize a posture of the pulse wave sensor 100.

The memory 104 is equivalent to the aforementioned memory 32, acquired data at the light sensor portions 101-1 to 101-n (i.e., raw data provided from the light sensor portions 101-1 to 101-n, or processed data which various kind of processes are performed at the controller 102) are stored by volatile or non-volatile method.

The wireless communication portion 105 is equivalent to the aforementioned wireless communication circuit 33, the measurement data acquired by using the light sensor portions 101-1 to 101-n (i.e., raw data provided from the light sensor portions 101-1 to 101-n, the processed data provided from the controller 102, or the stored data provided from the memory 104) are transmitted wirelessly to a personal computer or a cell phone of outside.

The power source portion 106 is equivalent to the aforementioned power source unit 20, and supplies power to each part of the pulse wave sensor 100.

The armlet type housing 107 is equivalent to the aforementioned armlet type housing 50 and contains the light sensor portions 101-1 to 101-n, the controller 102, the acceleration sensor portion 103, the memory 104, and the wireless communication portion 105.

Figure 17:
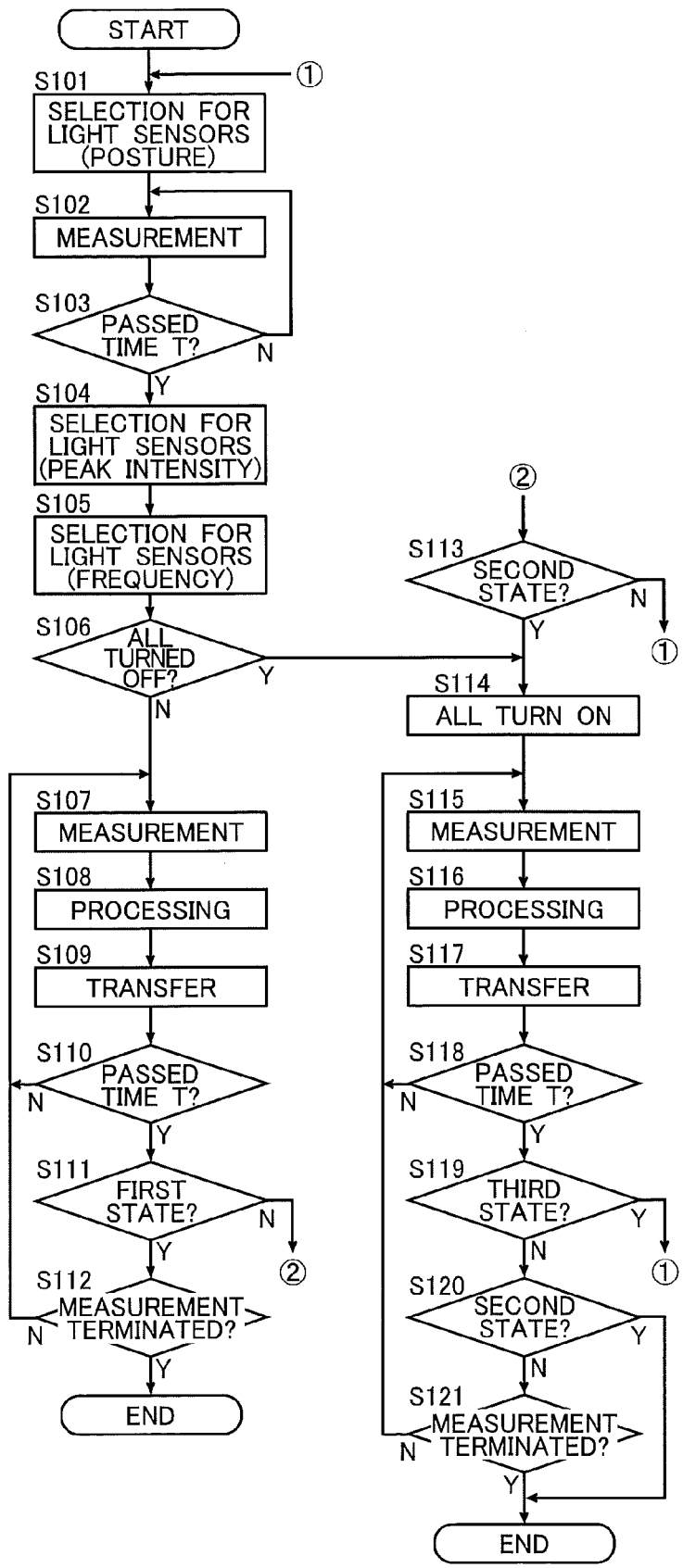
FIG. 17 is a flow chart illustrating an example of the pulse wave measurement operation of the pulse wave sensor 100.

FIG. 17 is a flow chart illustrating an example of the pulse wave measurement operation of the pulse wave sensor 100. In addition, the main body of execution of the flow chart is the controller 102 basically.

In step S101, posture of the pulse wave sensor 100 is recognized according to an output of the acceleration sensor portion 103, and ON/OFF control of the light sensor portions 101-1 to 101-n are performed based on the recognition result.

Figure 18:
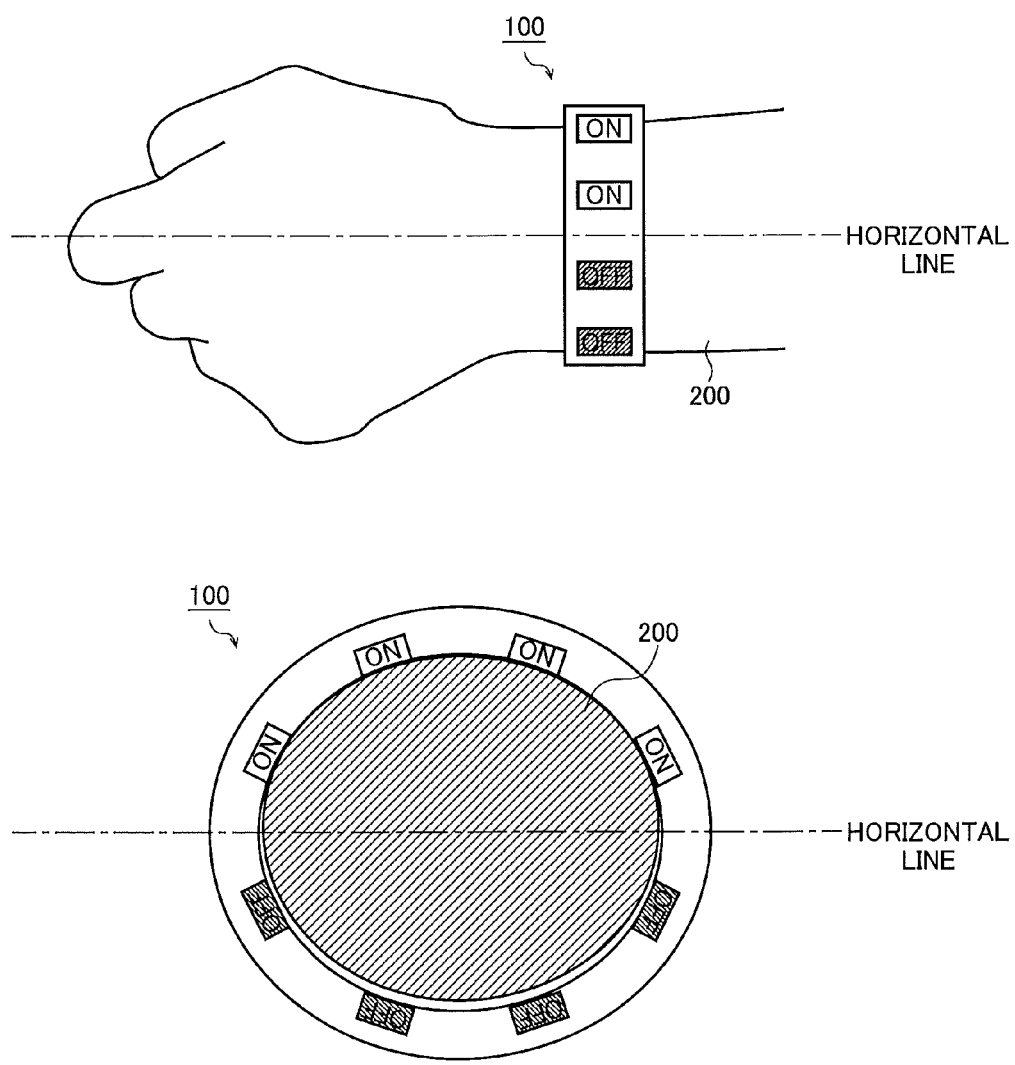
FIG. 18 is a schematic diagram to explain a light sensor selection operation at step S101 (horizontal).

For example, as illustrated in FIG. 18, in the case of the shaft center of the armlet type housing 107 is facing to the horizontal direction or horizontal direction approximately, according to its own weight of the armlet type housing 107, among the light sensor portions 101-1 to 101-n, the light sensor portions positioned above than the horizontal line which passes the center shaft are closely contacted to the wrist 200, and the sensors located beneath the horizontal line are apart from the wrist 200. Therefore, by turning ON the above positioned light sensor portions which are expected to perform normal pulse wave measurement, and turning OFF the beneath positioned light sensor portions which are not expected to perform normal pulse wave measurement in advance, the energy consumption can be reduced to ½ compared to all of the light sensor portions 101-1 to 101-n are turned ON without worsening the measurement accuracy of the pulse wave sensor 100.

Figure 19:
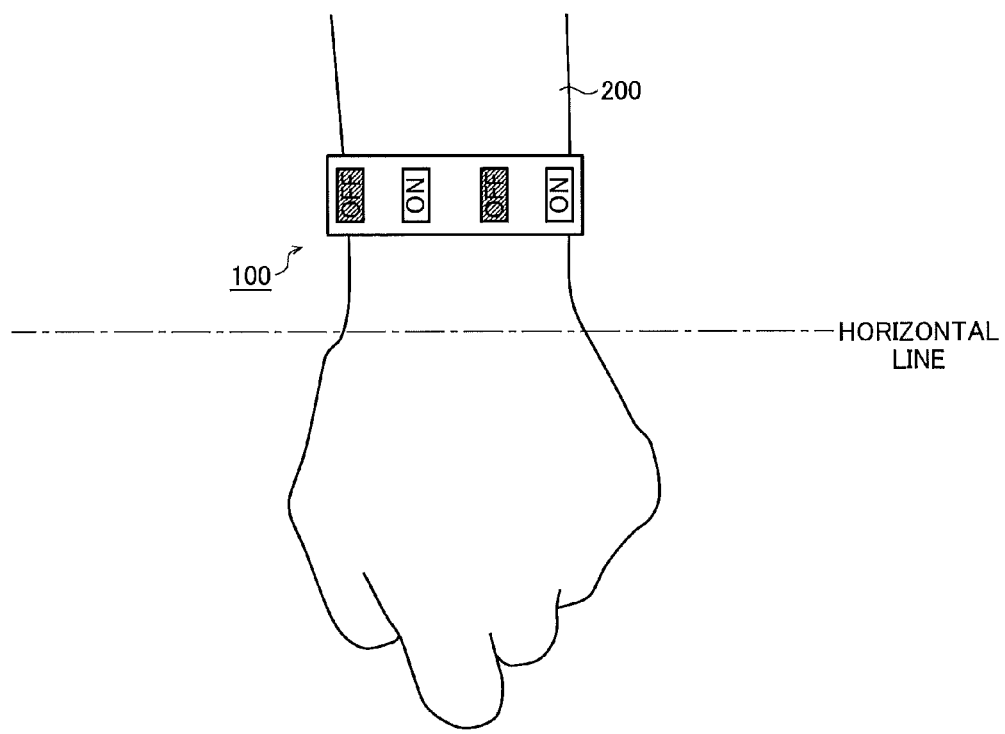
FIG. 19 is a schematic diagram to explain a light sensor selection operation at step S101 (vertical).
Figure 19:
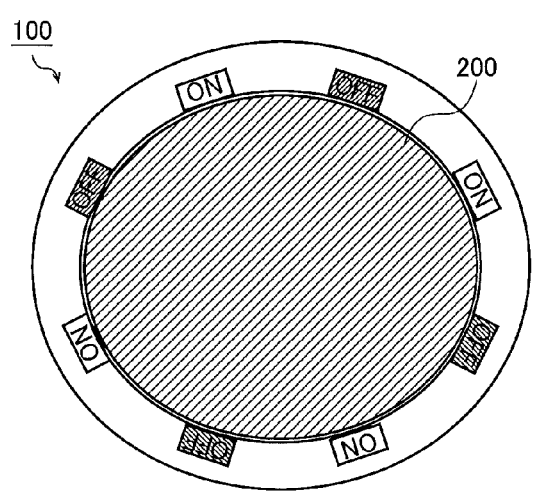

As illustrated in FIG. 19, in the case of shaft sensor of the armlet type housing 107 is facing to vertical direction or vertical direction approximately, it is not clear that any one of the light sensor portions 101-1 to 101-n is closely contacted to the wrist 200. Therefore, by means of turning ON and OFF the light sensor portions 101-1 to 101-n alternatively along with the circumferential direction of the armlet type housing 107, the energy consumption can be reduced to ½ compared to all of the light sensor portions 101-1 to 101-n are turned ON without worsening the measurement accuracy of the pulse wave sensor 100.

In step S102, among the light sensor portions 101-1 to 101-n, by using the light sensor turned ON in step S101, a measurement is performed to detect the intensity and the frequency of the output peak. With respect to the pulse wave measurement in this step, it is performed to acquire information required to select the light sensor portion furthermore, and transmission of the measured date to the outside is not performed.

In step S103, a judgment is performed whether or not a predetermined period T has passed since the pulse wave began in step S102. If judged as YES, the flow is proceeded to step S104, if judged as NO, the flow is returned to step S102. In addition, with respect to the aforementioned predetermined period T, it should be set long enough to detect the intensity and frequency of the output peak (in reference to FIG. 20).

In step S104, with respect to the measurement data measured by each of the light sensors portion which is turned ON in step S101 among the light sensor portions 101-1 to 101-n, each output intensity and predetermined threshold value are compared, based on the comparison result, ON/OFF control of each of the light sensor portions 101-1 to 101-n is performed. To be more concrete, with respect to the data whose output intensity is below than the predetermined threshold, the light sensor portion is turned OFF as interpreted output shortage is occurred.

Figure 20:
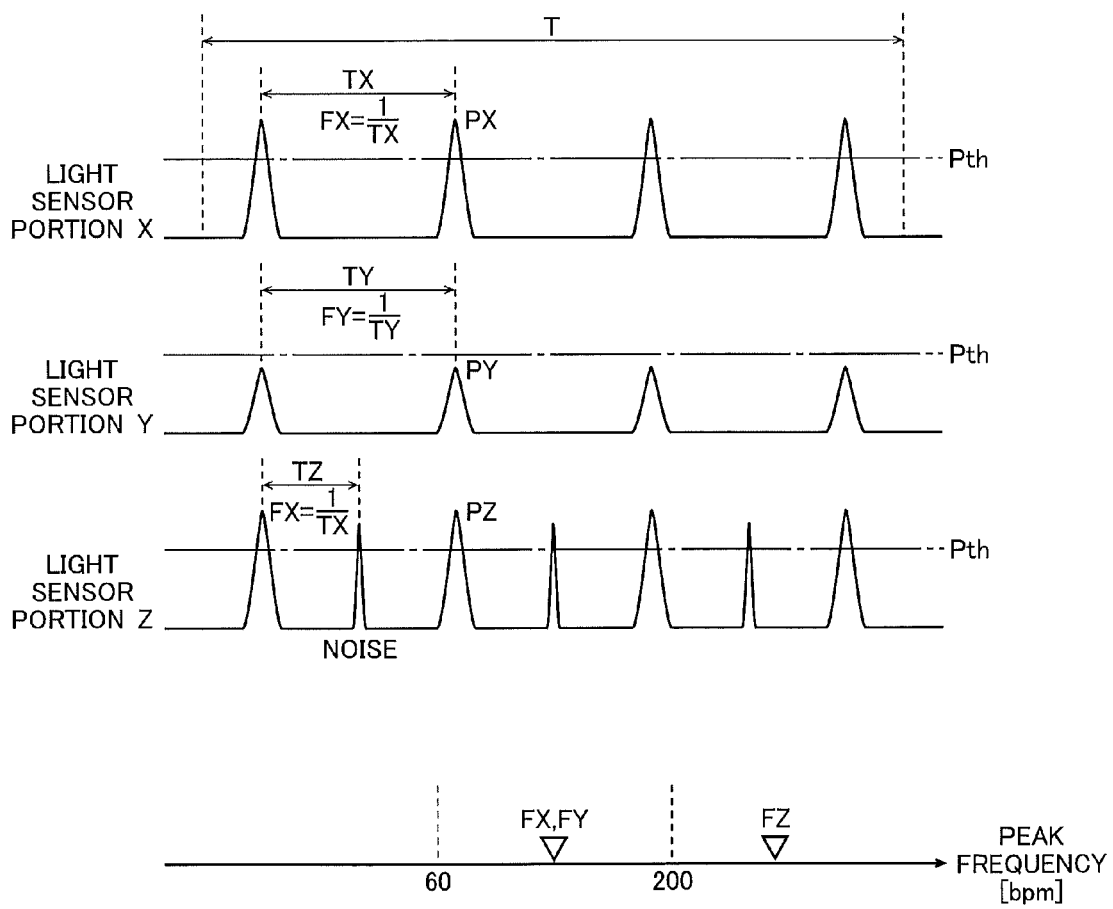
FIG. 20 is a diagram to explain a light sensor selection operation at step S104 and S105.

For example, among the illustrated light sensor portions X to Z in FIG. 20, with respect to the measured data of the light sensor portions X and Z, though the intensities PX and PZ of the output peak are higher than the threshold value Pth, with respect to the measurement data of the light sensor portion Y, the intensity PY of the output peak is lower than the threshold value Pth. Therefore, by turning OFF the light sensor portion Y which cannot be expected to measure the pulse wave normally, further reduction of the energy consumption can be realized without worsening the measurement accuracy of the pulse wave.

In step S105, with respect to the measurement data measured by each of the light sensors portion which is turned ON in step S101 among the light sensor portions 101-1 to 101-n, a judgment whether or not the frequency of each output peak is within the predetermined range is performed, based on the judgment result, ON/OFF control of each of the light sensor portions 101-1 to 101-n is performed. To be more concrete, with respect to its frequency of output peak is not within the range of 60 bpm to 200 bpm [beats per minutes], the light sensor portion is turned OFF as interpreted frequency abnormality (e.g., noise superimpose, etc) is occurred.

For example, among the light sensor portions X to Z in FIG. 20, with respect to the measurement data of the light sensor portions X and Y, though the frequencies FX and FY of output peak are within the predetermined range, with respect to the measurement data of the light sensor portion Z, the frequency FZ of output peak is not within the predetermined range because of the noise. Therefore, by turning OFF the light sensor portion Z which is not expected to measure the pulse wave normally in advance, further reduction of the energy consumption can be realized without worsening the measurement accuracy of the pulse wave.

In addition, with respect to the example in FIG. 20, among the light sensor portions X to Z, the light sensor portion Y is turned OFF in step S104 and the light sensor portion Z is turned OFF in step S105, only the light sensor portion X is remained as turned ON finally.

In step S106, by selection process for the light sensor portions in step S101 to S105, a judgment whether or not all of the light sensor portions 101-1 to 101-n are turned OFF is performed. If judged as NO here (i.e., in the case of at least one of the light sensor portions 101-1 to 101-n is remained as turned ON finally), the flow is proceeded to step S107. On the other hand, the flow is proceeded to step S114 if judged as YES.

In step S107, among the light sensor portions 101-1 to 101-n, after the selection process for the light sensor portions in step S101 to S105, the pulse wave is measured by using the light sensor portion which is remained as turned ON finally.

Figure 21:
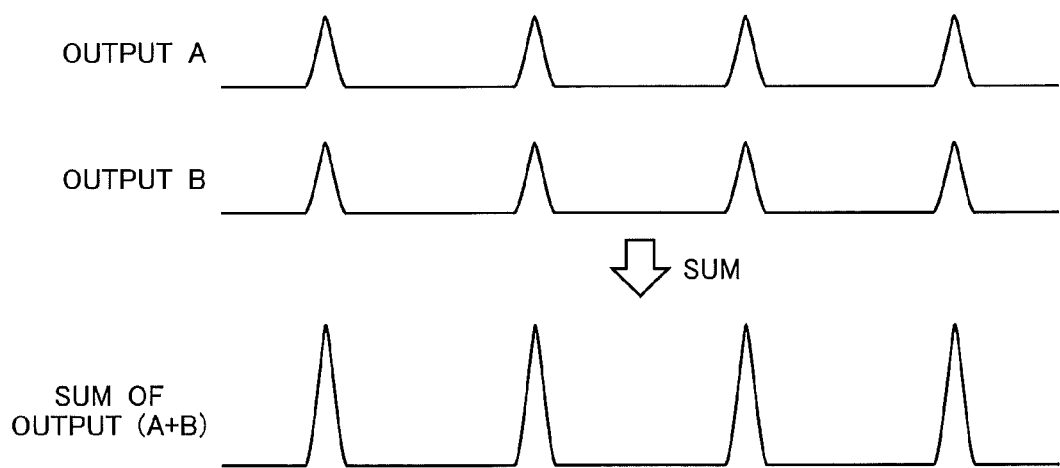
FIG. 21 is a diagram to explain a processing operation at step S108 (addition).

In step S108, a predetermined operation process is processed to the measurement data acquired in step S107. For example, as illustrated in FIG. 21, a method can be considered to generate an added output (i.e., A+B) by adding an output A of the light sensor portion A and an output B of the light sensor portion B. Owing to performing this operation process, S/N ratio can be improved by enhancing the intensity of the output peak.

Figure 22:
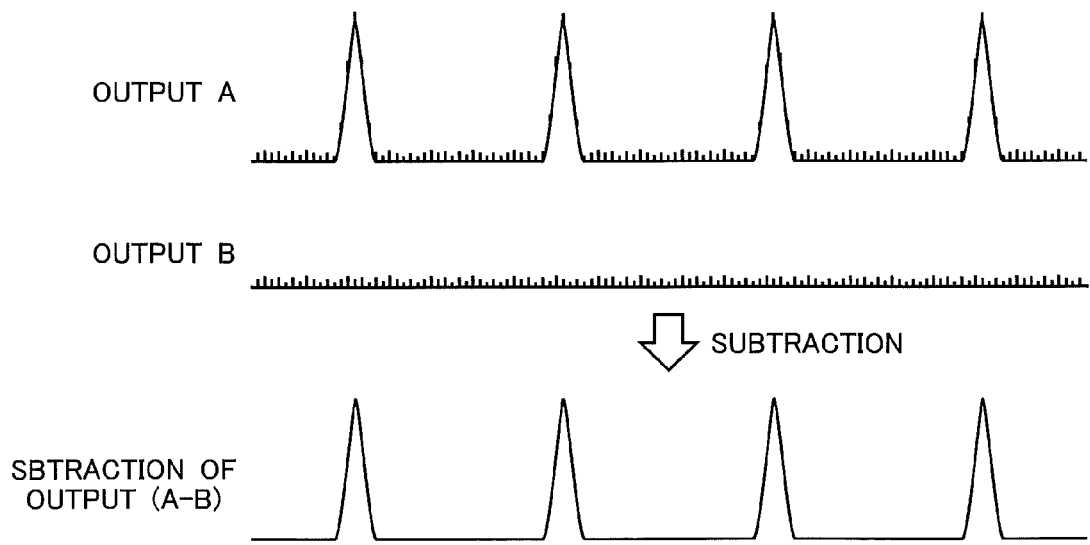
FIG. 22 is a diagram to explain a processing operation at step S108 (subtraction).

Moreover, as illustrated in FIG. 22, a method can be considered to generate the subtracted output (i.e., A-B) by subtracting the output B including only the noise component (i.e., an output of the light sensor B which is provided additionally to detect only for the dark current) from the output A of the light sensor portion A which a noise component is superimposed. Owing to performing this operation process, the noise component can be removed and S/N ratio can be improved.

In addition, with respect to the operation process in step S108, in addition to the aforementioned addition process and subtraction process, a selection process for the measurement data as selecting the largest intensity of the output peak among the multiple measurement data and providing the selected data is included.

In step S109, the generated measurement data after the operation process in step S108 is transferred to the outside personal computer or the cell phone. In addition, with respect to this flow chart, though a construction to transfer the measurement data in every time measuring the pulse wave is illustrated, the construction of the invention is not restricted to this, a construction can be adopted to perform batch transfer for the measurement data stored in every predetermined period (or the timing for terminating the pulse wave measurement) based on a temporal storing process for the measurement data in step S109.

In step S110, a judgment is performed whether or not a predetermined period T has passed since the pulse wave began in step S107. If judged as YES, the flow is proceeded to step S111, if judged as NO, the count result of the predetermined period T is being reset and the flow is returned to step S107

In addition, with respect to the aforementioned predetermined period T, it should be set long enough to detect the intensity and frequency of the output peak (in reference to FIG. 20).

Figure 23:
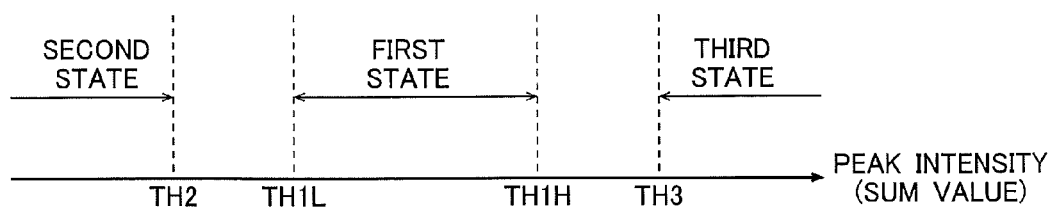
FIG. 23 is a diagram illustrating a definition example of first to third states.

In step S111, a judgment is performed whether or not the pulse wave sensor 100 is in the first state. The aforementioned first state is a state where the pulse wave is measured normally, to be more concrete, as illustrated in FIG. 23, it is expressed as the intensity of the output peak (i.e., added value if the multiple light sensor portions are turned ON) is larger than the first lower threshold value TH1L and smaller than the first upper threshold value TH1H (TH1L<TH1H). If judged as YES, the flow is proceeded to step S112, and if judged as NO, the flow is proceeded to step S113.

In step S112, a judgment is performed whether or not the pulse wave measurement termination is directed. If judged as YES, the aforementioned series of flows are terminated, and if judged as NO, the flow is returned to step S107.

In step S112, a judgment whether or not the pulse wave sensor 100 is in the second state. The second state is a state where the pulse wave can not be measured normally without turning ON all of the light sensor portions 101-1 to 101-n, to be more concrete, as illustrated in FIG. 23, it is expressed as the intensity of the output peak (added value if the multiple light sensor portions are turned ON) is smaller than the second threshold value TH2 (TH2<TH1L). If judged as YES, the flow is proceeded to step S114. On the other hand, if judged as NO, the flow is proceeded to step S101 and selection process for the light sensor portions 101-1 to 101-n is performed again from the beginning.

If judged as YES in step S106 or step S113, regardless of the selection process result for the light sensor portions 101-1 to 101-n in step S101 to S105, all of the light sensor portions 101-1 to 101-n are turned ON in step S114. Owing to this construction, it is possible to prioritize for enhancing the accuracy (i.e., stabilization) of the pulse wave than the reduction of the energy consumption.

In step S115, the pulse wave is measured by using all of the light sensor portions 101-1 to 101-n.

In step S116, a predetermined process is performed to the measurement data in step S115. With respect to this operation process, same as the aforementioned step S108, a redundant explanation is omitted here.

In step S117, the measurement data generated after the operation process in step S116 is transferred to the outside personal computer or the cell phone.

In step S118, a judgment is performed whether or not a predetermined period T has passed since the pulse wave measurement begun in step S115. If judged as YES, the flow is proceeded to step S111, and if judged as NO, the count result of the predetermined period T is being reset and the flow is returned to step S115.

In step S119, a judgment is performed whether or not the pulse wave sensor 100 is in the third state. The aforementioned third state is a state where the pulse wave is measured normally without turning ON all of the light sensor portions 101-1 to 101-n, to be more concrete, as illustrated in FIG. 23, it is expressed as the intensity of the output peak (i.e., added value if the multiple light sensor portions are turned ON) is larger than the third threshold value TH3 (TH3>TH1H). If judged as NO, the flow is proceeded to step S120. On the other hand, if judged as YES, the flow is proceeded to step S101 and selection process for the light sensor portions 101-1 to 101-n is performed again from the beginning.

In step S120, a judgment is performed whether or not the pulse wave sensor 100 is in the second state. The aforementioned second state is a state where the pulse wave can not be measured normally unless all of the light sensor portions 101-1 to 101-n are turned ON, to be more concrete, as illustrated in FIG. 23, it is expressed as the intensity of the output peak (i.e., added value if the multiple light sensor portions are turned ON) is smaller than the second threshold value TH2 (TH2<TH1L). If judged as NO, the flow is proceeded to step S121. On the other hand, if judged as YES, the sequential flow is terminated based on a judgment that it is impossible to measure the pulse wave normally anymore.

In step S121, a judgment is performed whether or not the pulse wave measurement termination is directed. If judged as YES, the aforementioned series of flows are terminated, if judged as NO, the flow is returned to step S115.

Figure 24:
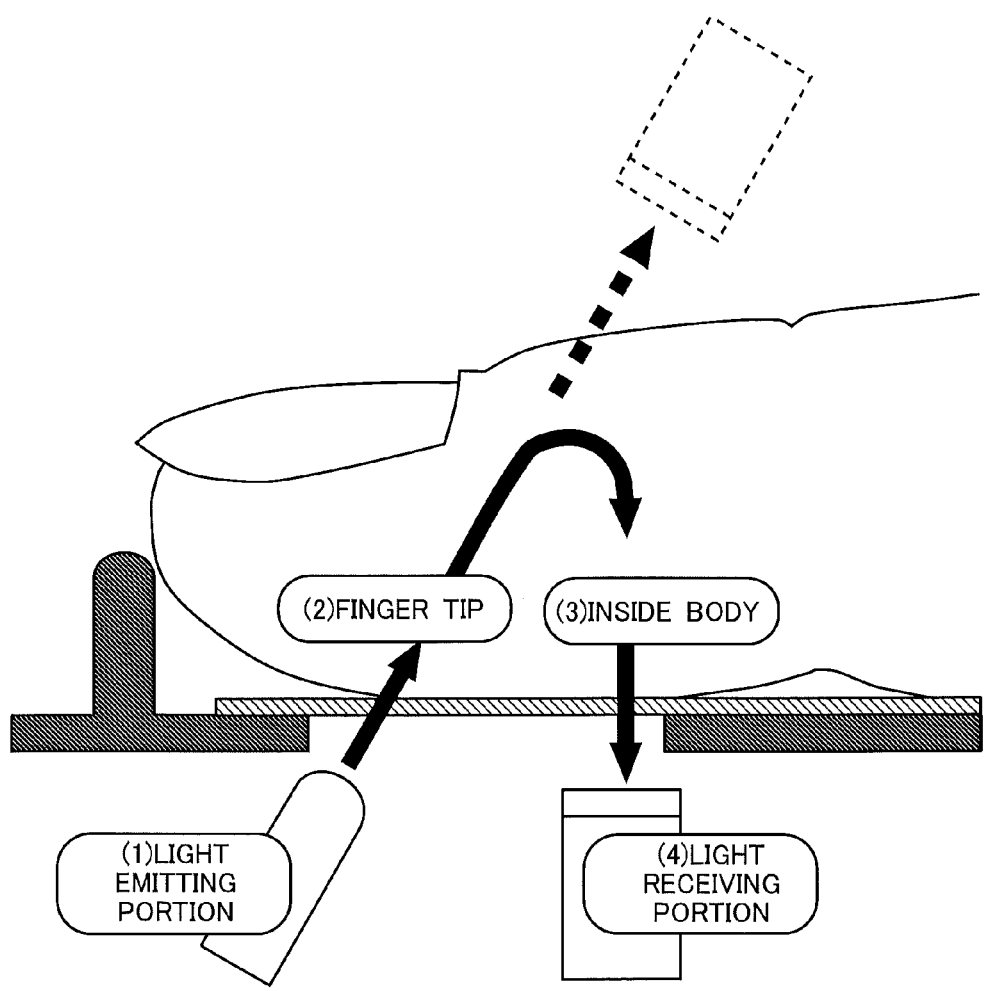
FIG. 24 is a schematic diagram to explain a principle of the pulse wave measurement in accordance with the implementation example 2 of the invention.

FIG. 24 illustrates a pulse wave sensor in accordance with the implementation example 2 to measure the pulse wave at fingertip. Even in case of detecting the pulse wave at fingertip, each of the basic principle of the pulse wave measurement and a situation where the amount of light attenuation within a living body (i.e., light absorption level) changes according to the time lapse can be understood based on the explanation of FIG. 1 and FIG. 2. However, "(2) wrist" in FIG. 1 should be substituted as "(2) fingertip" in FIG. 24 and understood as thus.

<A Block Diagram>

Figure 25:
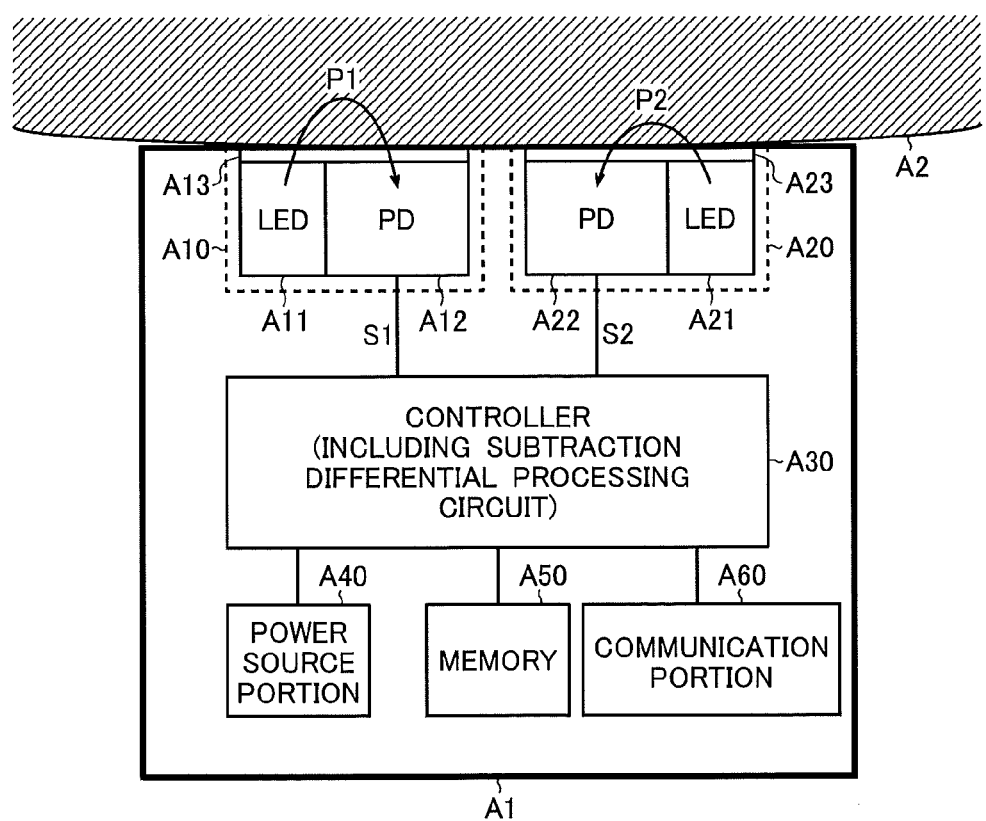
FIG. 25 is a block diagram illustrating a construction example of the pulse wave sensor in accordance with the implementation example 2.

FIG. 25 is a block diagram illustrating a construction example of the pulse wave sensor in accordance with the implementation example 2. The pulse wave sensor A1 of this construction example includes a first light sensor A10, a second light sensor A20, a controller A30, a power source portion A40, a memory portion A50, and a communication portion A60.

The first light sensor A10 is a light sensor to detect the pulse wave component mainly and includes the first light emitting portion A11, the first light receiving portion A12, and the measurement window A13. The first light emitting portion A11 emits a light of the first emission intensity P1 to the living body A2. As the first light emitting portion A11, a visible light LED or a near-infrared LED can be used. The first light receiving portion A12 receives a returned light emitted from the first light emitting portion A11 and penetrates the living body A2 and generates a first light receiving signal S1. As the first light receiving portion A12, a photo diode or a photo transistor can be used. The measurement window A13 is a translucency member (i.e., a glass plate or an acrylic plate) which is provided on the light emitting/receiving surface of the first light sensor A10. The first light sensor A10 performs the pulse wave measurement (i.e., light emission to the living body A2 and a detection of the returned light from the living body A2) via the measurement window A13. In addition, with respect to the thickness of the measurement window A13, it is desirable to design appropriately in view of the depth of focus of the first light sensor A10.

The second light sensor A20 is a light sensor to detect the motion noise component mainly and includes the second light emitting portion A21, the second light receiving portion A22, and the measurement window A23. The second light emitting portion A21 emits a light of the second emission intensity P2 weaker than the first emission intensity P1 to the living body A2. As the second light emitting portion A21, same as the first light emitting portion A11, the visible light LED or the near-infrared LED can be used. The second light receiving portion A22 receives a returned light emitted from the second light emitting portion A21 and penetrates the living body A2 and generates a second light receiving signal S2. As the second light receiving portion A22, same as the first light receiving portion A12, a photo diode or a photo transistor can be used. The measurement window A23 is a translucency member (i.e., a glass plate or an acrylic plate) which is provided on the light emitting/receiving surface of the second light sensor A20. The second light sensor A20 performs the pulse wave measurement (i.e., light emission to the living body A2 and a detection of the returned light from the living body A2) via the measurement window A23. In addition, with respect to the thickness of the measurement window A23, it is desirable to design appropriately in view of the depth of focus of the second light sensor A20.

In addition, with respect to the first light sensor A10 and the second light sensor A20, both of them are not a construction which both the light emitting portion and light receiving portion are not provided at the opposite side against the living body A2 (i.e., a so-called penetration type, in reference to a broken line arrow in FIG. 24), the pulse wave sensor has a construction both the light emitting portion and the light receiving portion are provided at same side against the living body A2 (i.e., a so-called reflection type, in reference to a full line arrow in FIG. 24). To detect the light emitted from the first light emitting portion A11 by the first light receiving portion A12 without fail, and to detect the light emitted from the second light emitting portion A21 by the second light receiving portion A22 without fail, it is desirable to adopt the reflection type which is insensitive to the light scattering in the living body A2 rather than the penetration type which is sensitive to the light scattering in the living body A2.

Moreover, the first light sensor A10 and the second light sensor A20 are located adjacent to each other. Owing to this construction, both the first light receiving signal S1 and the second light receiving signal S2 can be measured at same place approximately, the effect of the motion noise cancel process by the later mentioned differential operation process can be improved.

Moreover, with respect to the first light sensor A10 and the second light sensor A20, the first light emitting portion A11 and the second light receiving portion A22 are located to keep a distance each other, and the second light emitting portion A21 and the first light receiving portion A12 are located to keep a distance each other. This construction makes it possible to detect the light emitted from the first light emitting portion A11 by the first light receiving portion A12 without fail, and to detect the light emitted from the second light emitting portion A21 by the second light receiving portion A22 without fail.

The controller A30 includes the differential processing circuit to acquire the pulse wave data S3 by subtracting the second light receiving signal S2 from the first light receiving signal S1. The influence and effect of this differential operation is described later. Moreover, the controller A30 also includes the CPU [Central Processing Unit] which controls entire operation of the pulse wave sensor A1 generally and acquires various information about the pulse wave (i.e., the fluctuation of the pulse wave, the heart rate, the fluctuation of the heart rate, and the acceleration pulse wave) by means of performing various signal processes for the pulse wave data S3.

The power source portion A40 is a circuit block to supply power to each part of the pulse wave sensor A1, including the battery as a lithium ion secondary battery or an electrical double layer capacitor, a voltage conversion circuit to convert the input voltage from the battery to a desirable output voltage, and the charge circuit to perform charge control of the battery. In this way, with respect to the pulse wave sensor A1 of battery drive type, there is no need to connect a power supply cable from outside during the measurement of the pulse wave, measurement of the pulse wave can be realized without restricting the behavior of the examinee. In addition, as the charge method for the battery, a contact method using the USB [Universal Serial Bus] cable, or a non-contact method as an electromagnetic induction method, an electric field connection method, or an electric field resonance method can be used.

The memory portion A50 stores the pulse wave data S3 acquired at the controller A30 (i.e., a raw data or a processed data various processes are performed) as volatile or non-volatile method. In addition, as the memory portion A50, a volatile RAM [Random Access Memory] or a non-volatile flash memory can be used appropriately. With respect to a construction which has a storing method for the pulse wave data S3, because accumulated data of the memory portion A50 can be transmitted to outside by means of the batch transmission in every predetermined period, it is possible to let the wireless communication portion A60 be a standby state intermittently, furthermore, the battery drive time of the pulse wave sensor A1 can be extended.

The wireless communication portion A60 transmits the pulse wave data S3 acquired at the controller A30 (i.e., the raw data, the processed data various processes are performed, or the stored data at memory portion A50) to the external personal computer or a cell phone. In addition, with respect to the wireless communication portion A60, the Bluetooth (the registered trademark) module IC can be used appropriately for example. Owing to such a construction, the wired connection is not required to transmit the pulse wave data S3 to the external apparatus, it makes possible to perform a real time transmission for the pulse wave data S3 without restricting the behavior of the examinee.

<A Differential Processing Circuit>

Figure 26:
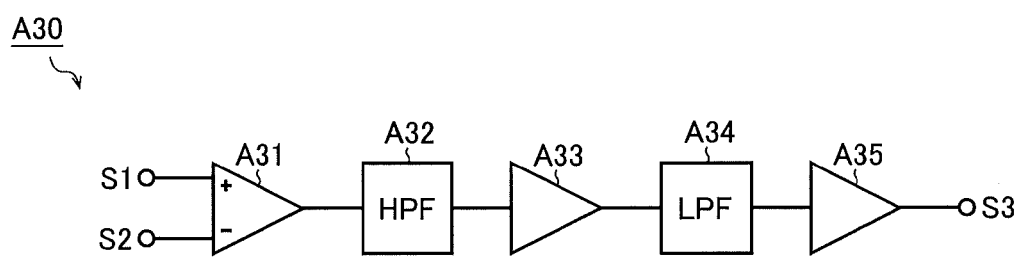
FIG. 26 is a block diagram illustrating a first construction example of a controller A30 (i.e., processing circuit).

FIG. 26 is a block diagram illustrating a first construction example of a controller A30 (differential processing circuit). The controller A30 (differential processing circuit) of the first construction example includes a differential amplifier A31, a high-pass filter (HPF) A32, a middle stage amplifier A33, a low-pass filter (LPF) A34, and a back stage amplifier A35. The differential amplifier A31 provides a differential signal between the first light receiving signal S1 to be provided to the non-inverted input terminal (+) and the second light receiving signal S2 to be provided to the inverted input terminal (−). The high-pass filter A32 cuts off a low frequency component (i.e., DC component) superimposed on the output signal of the differential amplifier A31 and provides it. The middle stage amplifier A33 amplifies an output signal of the high-pass filter A32 and provides it. The low-pass filter A34 cuts off a high frequency component (i.e., high frequency noise component) superimposed at the output signal of the middle stage amplifier A33 and provides it. The back stage amplifier A33 amplifies an output signal of the low-pass filter A34 and provides it. The output signal of the back stage amplifier A35 becomes the pulse wave data S3.

Figure 27:
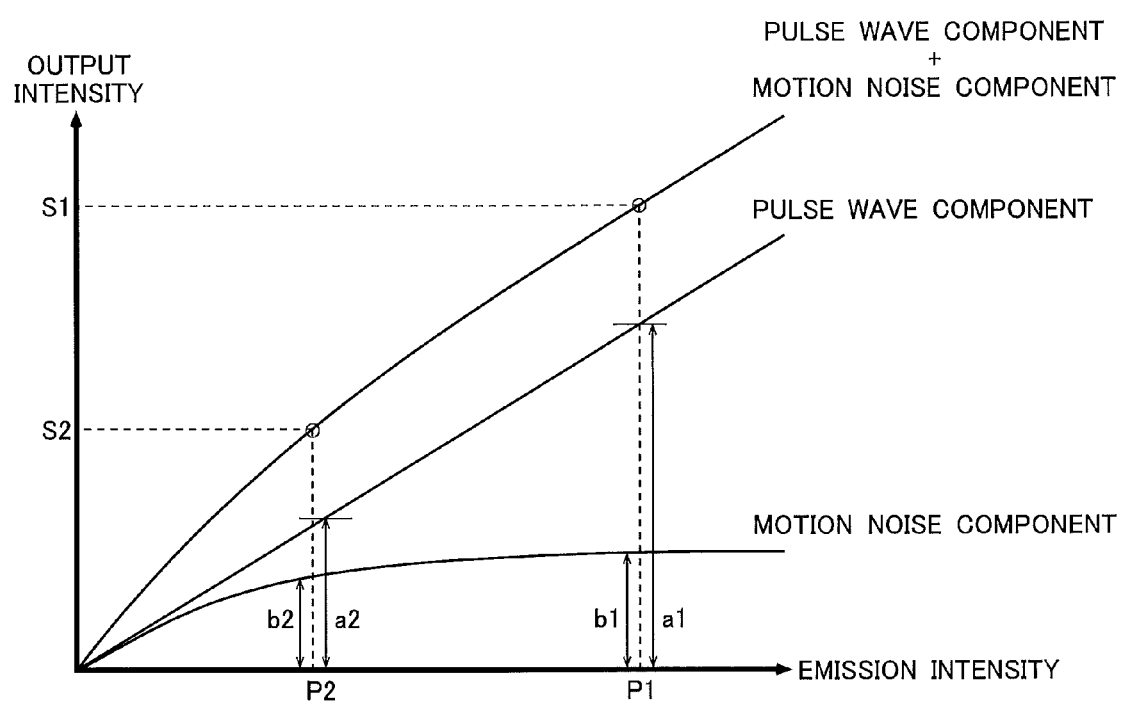
FIG. 27 is a correlation diagram illustrating a relationship between light emission intensity and output intensity.

FIG. 27 is a correlation diagram illustrating a relationship between light emission intensity and output intensity. As illustrated in FIG. 27, the pulse wave component and the motion noise component are included to each of the first light receiving signal S1 and the second light receiving signal S2. Here, the inventor of this application gets new knowledge that there is a difference of sensitivity against the light emission alternation about the relationship between the pulse wave component and the motion noise component, based on the dedicated examination. To be more concrete, the sensitivity of the pulse wave component is high against the light emission intensity alternation, the higher the light emission intensity is enhanced, the larger the pulse wave component included in the light receiving signal becomes (in reference to a1 and a2 in FIG. 27). On the other hand, because the sensitivity of the motion noise component is low against the light emission intensity alternation, the motion noise component included in the light receiving signal does not become so large even if the light emission intensity is enhanced (in reference to b1 and b2 in FIG. 27).

Figure 28:
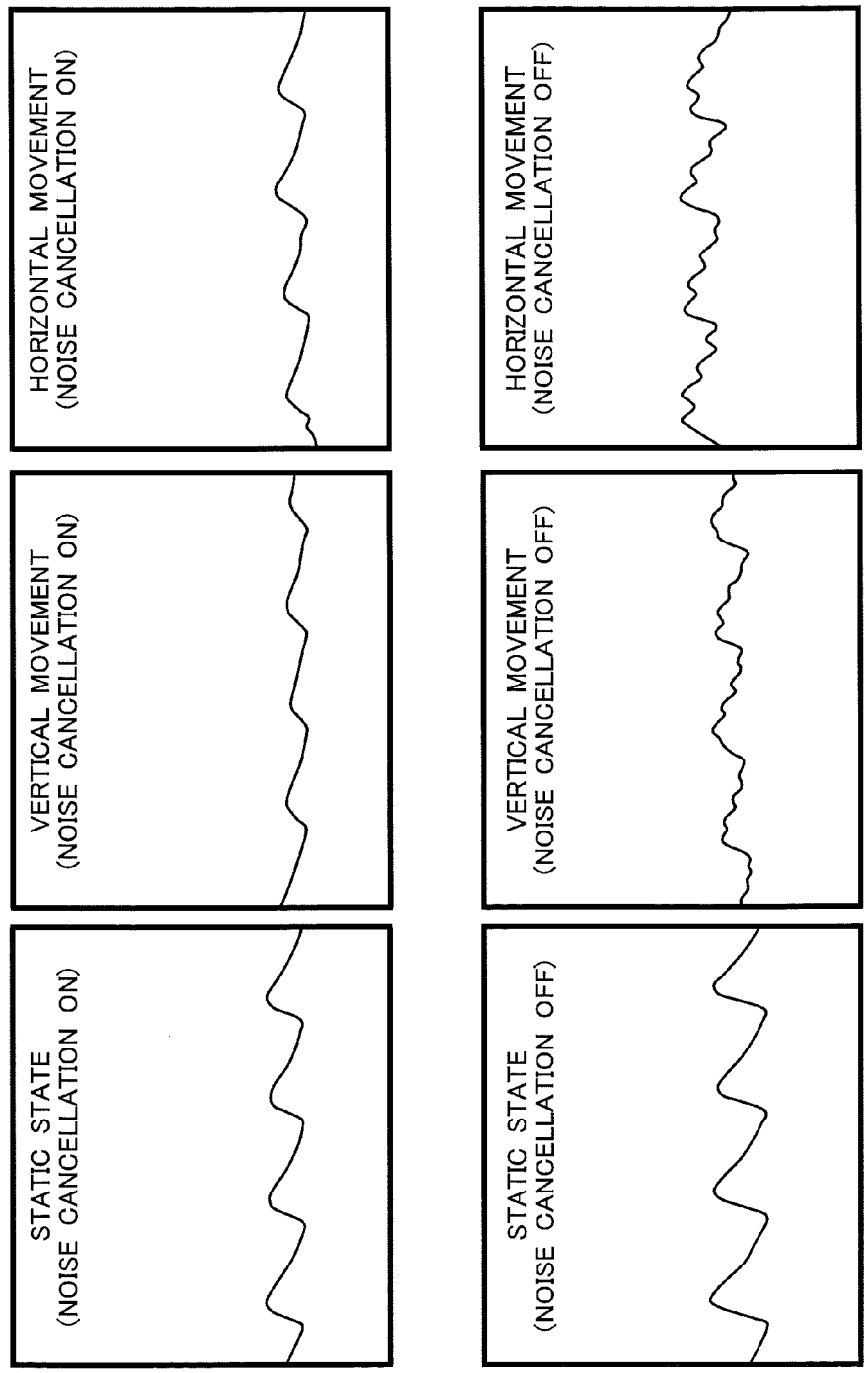
FIG. 28 is a wave form diagram illustrating an effect of a noise cancel operation process.

Therefore, by subtracting second light receiving signal S2 acquired at the second light sensor A20 of relatively week second light emission intensity P2 from the first light receiving signal S1 acquired at the first light sensor A10 of the first light emission intensity P1, the motion noise included in respective signals can be counterbalanced, then pure pulse wave component can be acquired (in reference to FIG. 28). Thus, with respect to the pulse wave sensor A1 in accordance with this construction example, regardless of the movement or vibration of the examinee, the pulse wave can be measured with high accuracy, the pulse wave can be measured all day long in daily life.

Figure 29:
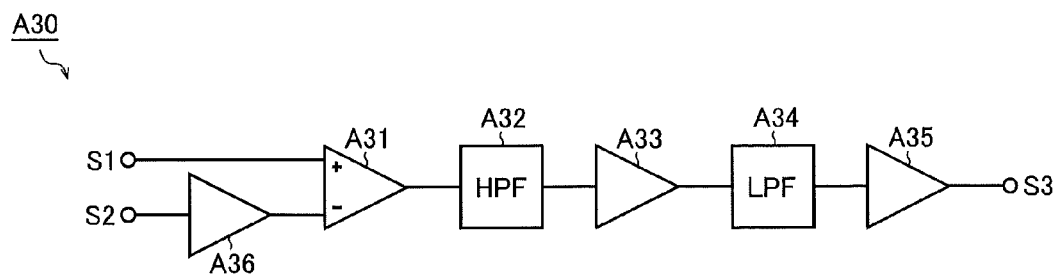
FIG. 29 is a block diagram illustrating a second construction example of a controller A30 (i.e., processing circuit).

FIG. 29 is a block diagram illustrating a second construction example of a controller 30 (i.e., differential processing circuit). The controller A30 (i.e., differential processing circuit) of the second construction example includes the front stage amplifier A36 besides the circuit elements A31 to A35 of the first construction example. The front stage amplifier A36 amplifies the second light receiving signal and provides it to the differential amplifier A31. Owing to this construction, according to adjusting the gain of the front stage amplifier A36 appropriately, the motion noise components included in the first light receiving signal S1 (in reference to b1 in FIG. 27) and the motion noise component included in the second light receiving signal S2 (in reference to b2 in FIG. 27) can be matched, then the effect of the motion noise cancellation can be exerted utmost.

<Various Applications>

[A Finger Bag Type]

Figure 30:
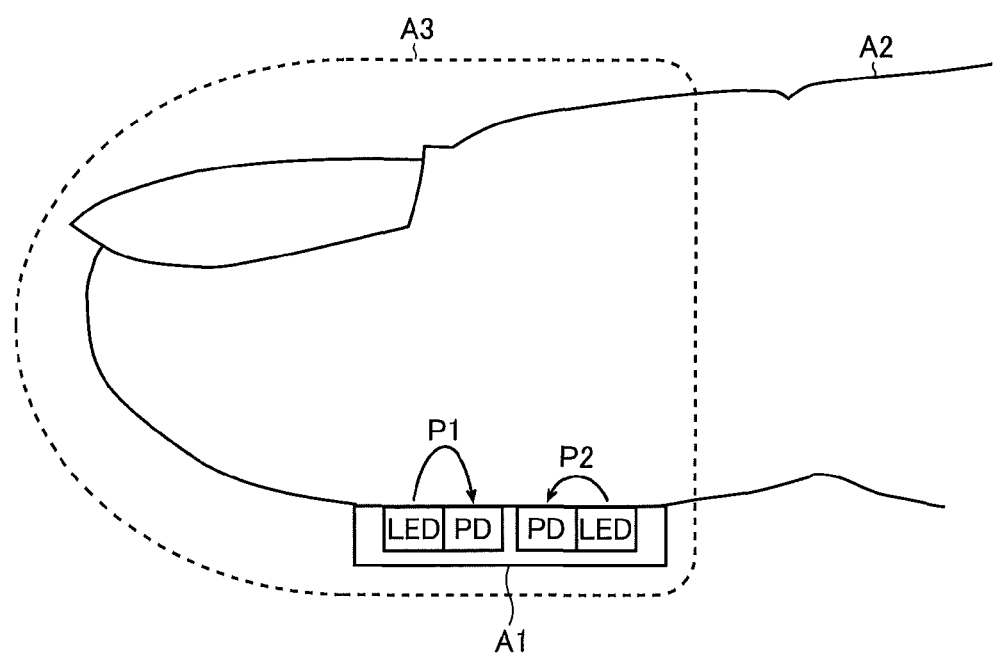
FIG. 30 is a schematic diagram illustrating a first application (i.e., finger bag type) of the pulse wave sensor A1.

FIG. 30 is a schematic diagram illustrating a first application (i.e., finger bag type) of the pulse wave sensor A1. With respect to the first application, the pulse wave sensor A1 includes a construction to measure the pulse wave at fingertip of the finger A2. To be more concrete, the pulse wave sensor A1 includes the finger bag construction to be worn on the tip of the finger A2 and measures the pulse wave measurement.

In addition, both the first light sensor A10 and the second light sensor A20 are contained within the housing A3 to be located to the ball side of the finger A2 (i.e., palm side) when the finger bag type housing A3 is worn on the tip of the finger A2. In this way, according to locating the first light sensor A10 and the second light sensor A20 at the ball side of the finger A2 (i.e., palm side) which is fleshy and whose fit feeling is fine, the stable measurement of the pulse wave can be performed. In this way, to improve the measurement accuracy is realized. Moreover, with respect to the first light sensor A10 and the second light sensor A20, they can be located aligned to a stretching direction of the finger A2. However, the location of the first light sensor A10 and the second light sensor A20 is not restricted to the aforementioned location.

Moreover, the housing A3 of the finger bag type works as light shielding member to cover the first light sensor A10 and the second light sensor A20. Owing to this construction, the pulse wave measurement can be measured steadily without effected by the external light.

[A Finger Ring Type]

Figure 31:
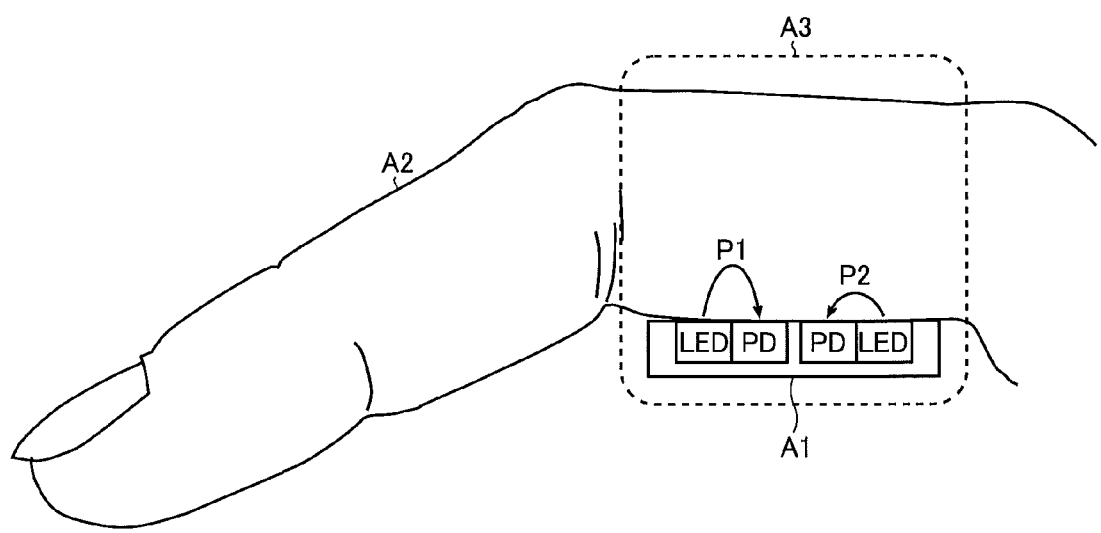
FIG. 31 is a schematic diagram illustrating a second application (i.e., finger ring type) of the pulse wave sensor A1.

FIG. 31 is a schematic diagram illustrating a second application (i.e., finger ring type) of the pulse wave sensor A1. With respect to the second application, the pulse wave sensor A1 includes a construction to measure the pulse wave at the third joint of the finger A2. To be more concrete, the pulse wave sensor A1 includes the finger ring construction to measure the pulse wave to be worn on the third joint of the finger A2.

In addition, both the first light sensor A10 and the second light sensor A20 are contained to the housing A3 to be located at the ball side (i.e., palm side) of the finger A2 when the finger ring type housing A3 is worn on the third joint of the finger A2. In this way, according to locating the first light sensor A10 and the second light sensor A20 at the ball side of the finger A2 (i.e., palm side) which is fleshy and whose fit feeling is fine, the stable measurement of the pulse wave can be performed. In this way, to improve the measurement accuracy is realized. Moreover, with respect to the first light sensor A10 and the second light sensor A20, they can be located aligned to a stretching direction of the finger A2, for example. However, the location of the first light sensor A10 and the second light sensor A20 is not restricted to the aforementioned location.

Moreover, the housing A3 of the finger ring type works as light shielding member to cover the first light sensor A10 and the second light sensor A20. Owing to this construction, the pulse wave measurement can be measured steadily without effected by the external light.

Moreover, with respect to the pulse wave sensor A1 including the finger ring construction, as long as the examinee does not take off the pulse wave sensor A1 from the finger A2 intentionally, because there is hardly any possibility to drop the pulse wave sensor A1 from the finger A2 when measuring the pulse wave, to measure the pulse wave without restricting the behavior of the examinee can be realized.

Moreover, with respect to the pulse wave sensor A1 of the finger ring construction, the consciousness of wearing the pulse wave sensor A1 can be reduced for the examinee, even in case of the continuous pulse wave measurement for a long period (i.e., few days to few months), excess stress can be avoided for the examinee.

[An Armlet Type]

Figure 32:
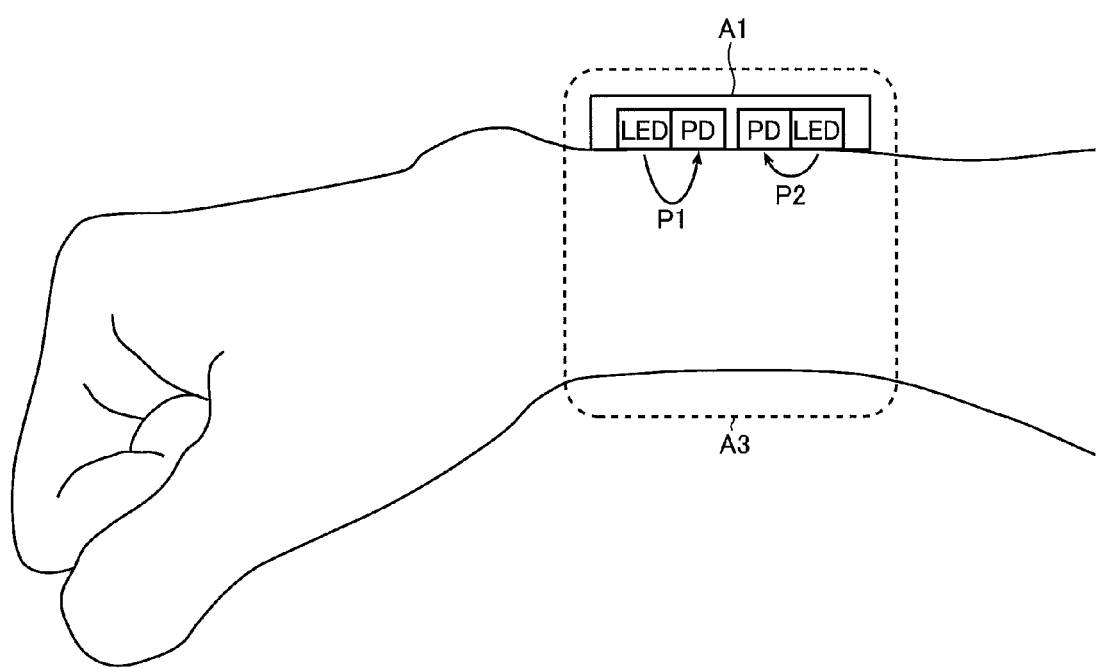
FIG. 32 is a schematic diagram illustrating a third application (i.e., armlet type) of the pulse wave sensor A1.

FIG. 32 is a schematic diagram illustrating a third application (i.e., armlet type) of the pulse wave sensor A1. With respect to the third application, the pulse wave sensor A1 includes a construction to measure the pulse wave at the wrist A2. To be more concrete, the pulse wave sensor A1 includes the armlet construction to measure the pulse wave to be worn on the wrist A2.

In addition, both the first light sensor A10 and the second light sensor A20 are contained to the housing A3 to be located at the back side (i.e., back side of the hand) of the wrist A2 when the armlet type housing A3 is worn on the wrist A2. In this way, according to locating the first light sensor A10 and the second light sensor A20 at the back side of the wrist A2 (i.e., back side of the hand) which is fleshy and whose fit feeling is fine, the stable measurement of the pulse wave can be performed. In this way, the accuracy for measuring the pulse wave can be improved. Moreover, with respect to the first light sensor A10 and the second light sensor A20, they can be located aligned to a stretching direction of the arm. However, the location of the first light sensor A10 and the second light sensor A20 is not restricted to the aforementioned location, both the first light sensor A10 and the second light sensor A20 can be located to both ends of the inside (i.e., palm side) of the wrist A2.

Moreover, the housing A3 of the armlet type works as light shielding member to cover the first light sensor A10 and the second light sensor A20. Owing to this construction, the pulse wave measurement can be measured steadily without effected by the external light.

Moreover, with respect to the pulse wave sensor A1 including the armlet construction, as long as the examinee does not take off the pulse wave sensor A1 from the wrist A2 intentionally, because there is hardly any possibility to drop the pulse wave sensor A1 from the wrist A2 when measuring the pulse wave, to measure the pulse wave without restricting the behavior of the examinee can be realized.

Moreover, with respect to the pulse wave sensor A1 of the armlet construction, the consciousness of wearing the pulse wave sensor A1 can be reduced for the examinee, even in case of the continuous pulse wave measurement for a long period (i.e., few days to few months), excess stress can be avoided for the examinee.

[An Eye Mask Type]

Figure 33:
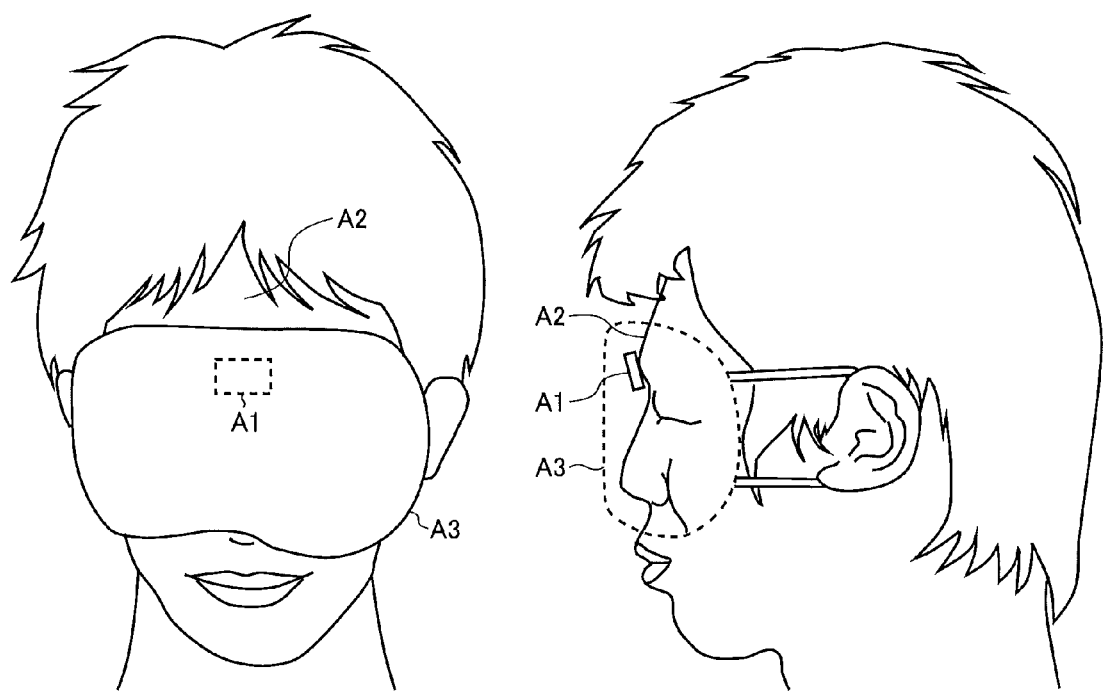
FIG. 33 is a schematic diagram illustrating a fourth application (i.e., eye mask type) of the pulse wave sensor A1.

FIG. 33 is a schematic diagram illustrating a fourth application (i.e., eye mask type) of the pulse wave sensor A1. With respect to the fourth application, the pulse wave sensor A1 includes a construction to measure the pulse wave at the head A2. To be more concrete, the pulse wave sensor A1 includes the eye mask construction to measure the pulse wave to be worn on head A2.

In addition, both the first light sensor A10 and the second light sensor A20 are contained to the housing A3 to be located at a position of the brow when the eye mask type housing A3 is worn on the head A2. In this way, according to locating the first light sensor A10 and the second light sensor A20 at brow where the blood capillary is gathered, the pulse wave can be measured steadily, the measurement accuracy of the pulse wave can be improved. Moreover, with respect to the first light sensor A10 and the second light sensor A20, they can be located aligned to the horizontal direction of the head A2 for example. However, the location of the first light sensor A10 and the second light sensor A20 is not restricted to the aforementioned location, both the first light sensor A10 and the second light sensor A20 can be located to the forehead, tip of the nose, the cheek, below the eye, the temple, or the ear lobe.

Moreover, the housing A3 of the eye mask type works as light shielding member to cover the first light sensor A10 and the second light sensor A20. Owing to this construction, the pulse wave measurement can be measured steadily without effected by the external light.

Moreover, with respect to the pulse wave sensor A1 with the eye mask construction, because the eye mask can relax the examinee based on the original function of its own, excess stress can be avoided for the examinee during the pulse wave measurement. Owing to this characteristic, the pulse wave sensor A1 of eye mask construction can be used as a pleasant sleeping sensor (i.e., a sensor to acquire information about sleeping state of the examinee from the pulse wave information) appropriately.

Figure 34:
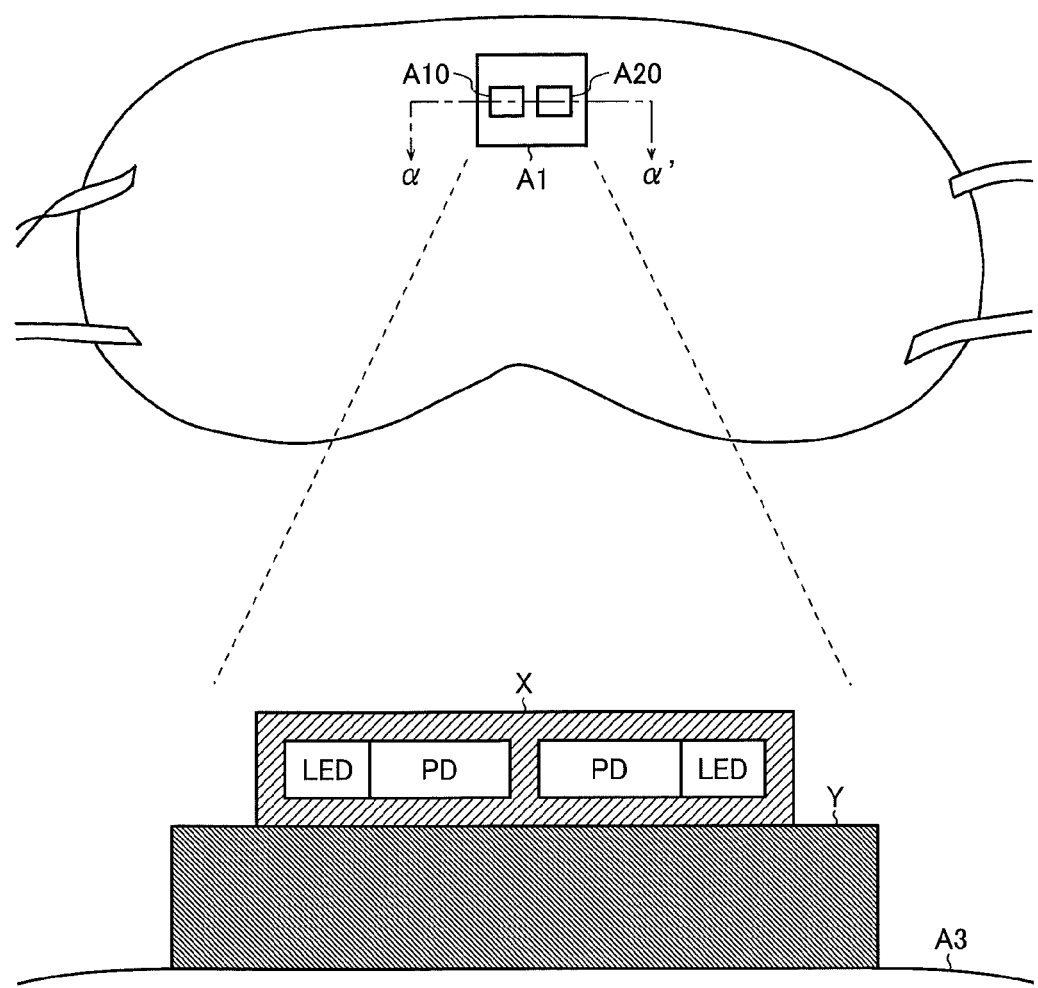
FIG. 34 is a schematic diagram illustrating a locating example of the pulse wave sensor A1 inside of the eye mask.

FIG. 34 is a schematic diagram illustrating a locating example of the pulse wave sensor A1 inside of the eye mask. As illustrated in FIG. 34, both the first light sensor A10 and the second light sensor A20 are covered by fit material as PDMS [polydimethylsiloxane] resin. Moreover, cushion element Y as a synthesized sponge is provided between the first light sensor A10 and the housing A3, and between the second light sensor A20 and the housing A3. Owing to this construction, because a characteristic of the close contact between the pulse wave sensor A1 and the living body A2 (i.e., head) can be improved, the pulse wave measurement can be performed steadily.

In addition, with respect to the output wave length of the light emitting portion, it is desirable to use the visible light region shorter than or equal to the wave length of 600 nm for the second implementation example, too. The reason is as told at consideration in the first implementation example.

<Another Implementation of the Second Implementation Example>

In addition, with respect to the aforementioned implementation, though the explanation is described as the output wave length of the first light emitting portion A11 and the second light emitting portion A21 are same as the prerequisite, the construction of the invention is not restricted to this, after setting different output wave lengths each other for the first light emitting portion A11 and the second light emitting portion A21, each of the light emission intensities can be set separately, accordingly.

Moreover, with respect to the aforementioned implementation, though an explanation is described based on an illustration of a construction provided with one first light sensor A10 to detect the pulse wave component mainly and one second light sensor A20 to detect the motion noise component mainly, the construction of this invention is not restricted to this, m (m is larger than or equal to 2) first light sensors A10 and n (n is larger than or equal to 2) second light sensors A20 can be provided.

<A Possibility for Industrial Application>

The technical features disclosed in this description can be used as techniques to improve a convenience of the pulse wave sensor. Applications to several fields as a health care support machine, a game machine, a music instrument, a pet communication tool, and a machine to prevent having a doze off while driving the car can be thought as possible.

<Other Variations>

With respect to the construction of the invention, in addition to the aforementioned implementations, various modifications can be made without departing from the spirit and the scope of the disclosure. In other words, the aforementioned implementations are just examples, and are not considered as restrictive. The technical scope of the disclosure should be determined based on the scope of the claims, not based on an explanation of the aforementioned implementations. It is understood that any variations within the scope of the claims and equivalents should be included to the scope of the technical scope of the disclosure, other implementations are within the scope of the claims.

LIST OF REFERENCE NUMERALS 1 pulse wave sensor
2 wrist
10, 10a-10h measurement unit
11 substrate
12 light sensor
13 measurement window (translucency member)
14 amplifier circuit
15 processing circuit (CPU)
20, 20x, 20y, 20a-20h power source unit
21 substrate
22 battery
23 power source circuit (DC/DC converter)
24 charge circuit
30, 30a-30h communication unit
31 substrate
32 memory
33 wireless communication circuit
40, 40x, 40y, 40a-40h cable
50 armlet type housing
60 display unit
61 main body portion
62 display portion
100 pulse wave sensor
101 to 101-n light sensor
102 controller
103 acceleration sensor portion
104 memory
105 wireless communication portion
106 power source portion
107 armlet type housing
200 wrist
A1 pulse wave sensor
A2 living body (finger (fingertip, third joint), wrist, head (brow))
A3 light shielding member (housing)
A10 first light sensor (for pulse wave detection)
A11 light emitting portion (LED)
A12 light receiving portion (PD)
A13 measurement window (translucency member)
A20 second light sensor (for motion noise detection)
A21 light emitting portion (LED)
A22 light receiving portion (PD)
A23 measurement window (translucency member)
A30 controller (including a differential processing circuit)
A31 differential amplifier
A32 high-pass filter (HPF)
A33 middle stage amplifier
A34 low-pass filter (LPF)
A35 back stage amplifier
A36 front stage amplifier
A40 power source portion
A50 memory portion
A60 communication portion
X fit material as PDMS (polydimethylsiloxane, etc]
Y cushion element Y (synthesized sponge, etc)

What is claimed is:

1. A pulse wave sensor comprising:
an armlet construction to be worn on a wrist of a living body and to measure a pulse wave, wherein the armlet construction comprises:
a plurality of measurement units to measure the pulse wave,
a plurality of power source units to supply power to respective ones of the measurement units,
one or more cables to connect electrically between respective ones of the measurement units and a corresponding one of the power source units,
a controller to perform ON/OFF control of each of the measurement units,
an acceleration sensor portion, and
an armlet type housing to contain the measurement units, the power source units and the one or more cables,
wherein the measurement units are equally spaced from one another around the armlet type housing, wherein each of the measurement units comprises a light sensor to detect an intensity of light emitted toward the wrist and penetrating a living body, and the number of the power source units is smaller than that of the measurement units, and power is supplied from each power unit to a different respective sub-group of the measurement units, and wherein, based on the output of the acceleration sensor portion, the controller controls some of the light measurement units to be ON, while others of the measurement units are OFF.

2. The pulse wave sensor according to claim 1, wherein each measurement unit comprises a light emitting portion, and wherein an output wavelength of the light emitting portion belongs to the visible light region and is smaller than or equal to 600 nm approximately.

3. The pulse wave sensor according to claim 1 further comprising:

a display unit provided at the armlet type housing to provide display information.

4. The pulse wave sensor according to claim 1 wherein the measurement unit comprises:

an amplifier circuit to amplify an output signal of the light sensor, and a processing circuit to acquire information related to the pulse wave based on the output signal of the amplifier circuit.

5. The pulse wave sensor according to claim 4 wherein the measurement unit comprises a substrate having a surface on which the light sensor is mounted and having a rear face on which the amplifier circuit and the processing circuit are mounted.

6. The pulse wave sensor according to claim 1 wherein the power source unit comprises:

a battery, and a power source circuit to convert an input voltage from the battery to an intended output voltage.

7. The pulse wave sensor according to claim 6, wherein the power source unit comprises a charge circuit to perform charge control of the battery.

8. The pulse wave sensor according to claim 7, wherein the charge circuit receives a power supply from outside by a contact method.

9. The pulse wave sensor according to claim 7, wherein the charge circuit receives a power supply from outside by a non-contact method.

10. The pulse wave sensor according to claim 1 further comprising: a communication unit to transfer the measurement data acquired by the measurement unit to the outside of the pulse wave sensor.

11. The pulse wave sensor according to claim 10 wherein the communication unit comprises:

a memory to store the measurement data, and a wireless communication circuit to transmit the measurement data wirelessly to the outside.

12. The pulse wave sensor according to claim 1, wherein the armlet type housing is a water-proof construction.

13. The pulse wave sensor according to claim 1, wherein the armlet type housing is made of an elastic element.

14. A pulse wave sensor comprising:

multiple light sensor portions to detect an intensity of light emitted to a wrist and penetrating a living body, a controller to perform ON/OFF control of each of the multiple light sensor portions, and an armlet type housing to contain the multiple light sensor portions and the controller, wherein the controller is configured to judge whether or not the frequency of each output peak of the multiple light sensor portions is within a predetermined range, and turn OFF particular ones of the multiple light sensor portions based on a judgment result which indicates that the particular light sensor portions have frequency abnormality.

15. A pulse wave sensor comprising:

multiple light sensor portions to detect an intensity of light emitted to a wrist and penetrating a living body, a controller to perform ON/OFF control of each of the multiple light sensor portions, an armlet type housing to contain the multiple light sensor portions and the controller, and an acceleration sensor portion, wherein, based on the output of the acceleration sensor portion, the controller controls some of the light sensor portions to be ON, while others of the light sensor portions are OFF.

* * * * *